US008206711B2

(12) United States Patent
White et al.

(10) Patent No.: US 8,206,711 B2
(45) Date of Patent: *Jun. 26, 2012

(54) TREATMENT OF CHRONIC LYMPHOCYTIC LEUKEMIA USING ANTI-CD20 ANTIBODIES

(75) Inventors: Christine A. White, Rancho Santa Fe, CA (US); Antonio J. Grillo-Lopez, Rancho Santa Fe, CA (US); John G. Curd, Hillsborough, CA (US); Susan Desmond-Hellmann, Alamo, CA (US)

(73) Assignees: Biogen Idec Inc., Cambridge, MA (US); Genentech, Inc., South San Francisco, CA (US)

( * ) Notice: Subject to any disclaimer, the term of this patent is extended or adjusted under 35 U.S.C. 154(b) by 7 days.

This patent is subject to a terminal disclaimer.

(21) Appl. No.: 12/629,472

(22) Filed: Dec. 2, 2009

(65) Prior Publication Data

US 2010/0080769 A1    Apr. 1, 2010

Related U.S. Application Data

(63) Continuation of application No. 09/436,347, filed on Nov. 9, 1999, now Pat. No. 7,682,612.

(60) Provisional application No. 60/107,658, filed on Nov. 9, 1998.

(51) Int. Cl.
*A61K 39/395* (2006.01)
*A61K 51/00* (2006.01)

(52) U.S. Cl. ............... 424/138.1; 424/1.49; 424/133.1; 424/143.1; 424/144.1; 424/153.1; 424/156.1; 424/174.1; 530/350; 530/387.1; 530/387.3; 530/387.7; 530/388.1; 530/388.2; 530/388.73; 530/388.8; 530/388.85; 530/391.3

(58) Field of Classification Search ........ 424/1.49, 424/133.1, 138.1, 143.1, 144.1, 153.1, 156.1, 424/174.1; 530/350, 387.1, 387.3, 387.7, 530/388.1, 388.2, 388.73, 388.8, 388.85, 530/391.3
See application file for complete search history.

(56) References Cited

U.S. PATENT DOCUMENTS

| | | | |
|---|---|---|---|
| 4,816,397 A | 3/1989 | Boss | |
| 4,816,567 A | 3/1989 | Cabilly | |
| 4,831,175 A | 5/1989 | Gansow | |
| 4,975,278 A | 12/1990 | Senter | |
| 5,099,069 A | 3/1992 | Gansow | |
| 5,124,471 A | 6/1992 | Gansow | |
| 5,225,539 A | 7/1993 | Winter | |
| 5,246,692 A | 9/1993 | Gansow | |
| 5,250,732 A | 10/1993 | Kogan | |
| 5,286,850 A | 2/1994 | Gansoh | |
| 5,439,665 A | 8/1995 | Hansen | |
| 5,441,871 A | 8/1995 | Seon | |
| 5,460,785 A | 10/1995 | Rhodes | |
| 5,500,362 A | 3/1996 | Robinson | |
| 5,530,101 A | 6/1996 | Queen | |
| 5,595,721 A | 1/1997 | Kaminski | |
| 5,648,267 A | 7/1997 | Reff | |
| 5,658,590 A | 8/1997 | Heiligenstein et al. | |
| 5,677,171 A | 10/1997 | Hudziak | |
| 5,677,180 A | 10/1997 | Robinson | |
| 5,686,072 A | 11/1997 | Uhr | |
| 5,691,135 A | 11/1997 | Braun | |
| 5,691,320 A | 11/1997 | von Borstel | |
| 5,693,627 A | 12/1997 | Schieven | |
| 5,693,780 A | 12/1997 | Newman | |
| 5,721,108 A | 2/1998 | Robinson | |
| 5,726,023 A | 3/1998 | Cheever | |
| 5,736,137 A | 4/1998 | Anderson | |
| 5,776,456 A | 7/1998 | Anderson | |
| 5,399,061 A | 12/1998 | Anderson | |
| 5,843,398 A | 12/1998 | Kaminski | |
| 5,843,439 A | 12/1998 | Anderson | |
| 6,015,542 A | 1/2000 | Kaminski | |
| 6,090,365 A | 7/2000 | Kaminski | |
| 6,120,767 A | 9/2000 | Robinson | |
| 6,183,744 B1 | 2/2001 | Goldenberg | |
| 6,287,537 B1 | 9/2001 | Kaminski et al. | |
| 6,306,393 B1 | 10/2001 | Goldenberg | |
| 6,399,061 B1 | 6/2002 | Anderson | |
| 6,399,649 B1 | 6/2002 | Lerner | |
| 6,455,043 B1 | 9/2002 | Grillo-Lopez | |
| RE38,008 E | 2/2003 | Abrams | |
| 6,565,827 B1 | 5/2003 | Kaminski | |
| 6,652,852 B1 | 11/2003 | Robinson | |
| 6,682,734 B1 | 1/2004 | Anderson | |
| 6,893,625 B1 | 5/2005 | Robinson | |
| 7,381,560 B2 | 6/2008 | Anderson | |
| 7,422,739 B2 | 9/2008 | Anderson | |
| 7,682,612 B1 | 3/2010 | White et al. | |
| 7,744,877 B2 | 6/2010 | Anderson et al. | |
| 2002/0009444 A1 | 1/2002 | Grillo-López | |
| 2002/0197255 A1 | 12/2002 | Anderson | |

(Continued)

FOREIGN PATENT DOCUMENTS

EP            0 173 494 A2    5/1986

(Continued)

OTHER PUBLICATIONS

Adams R.A. *Cancer Res.* 27: 2479-82, 1967. Formal discussion: the role of transplantation in the experimental investigation of human leukemia and lymphoma. Adams R.A. et al. *Cancer Res.* 28(6): 1121-25, 1968. Direct implantation and serial transplantation of human acute lymphoblastic leukemia in hamsters, SB-2.

Alas S. et al. *Anticancer Res.* 20(5A): 2961-66, 2000. Potentiation of fludarabine cytotoxicity on non-Hodgkin's lymphoma by pentoxifylline and rituximab.

Alas S. et al. *Clin. Cancer Res.* 7(3): 709-23, 2001. Inhibition of interleukin 10 by rituximab results in down-regulation of bcl-2 and sensitization of B-cell non-Hodgkin's lymphoma to apoptosis.

(Continued)

*Primary Examiner* — Alana H Dent
(74) *Attorney, Agent, or Firm* — Sidley Austin LLP

(57) ABSTRACT

Chronic Lymphocytic Leukemia (CLL) may be treated with antibodies directed against the CD20 antigen.

9 Claims, No Drawings

U.S. PATENT DOCUMENTS

| | | |
|---|---|---|
| 2003/0018014 A1 | 1/2003 | Lerner |
| 2003/0021781 A1 | 1/2003 | Anderson et al. |
| 2003/0026804 A1 | 2/2003 | Grillo-López |
| 2003/0082172 A1 | 5/2003 | Anderson |
| 2003/0095963 A1 | 5/2003 | Anderson |
| 2003/0147885 A1 | 8/2003 | Anderson |
| 2003/0206903 A1 | 11/2003 | Grillo-López |
| 2004/0056312 A1 | 7/2004 | Adams |
| 2004/0167319 A1 | 8/2004 | Teeling |
| 2004/0213784 A1 | 10/2004 | Grillo-López |
| 2005/0163708 A1 | 7/2005 | Robinson |
| 2005/0186205 A1 | 8/2005 | Anderson |
| 2006/0034835 A1 | 2/2006 | Adams |
| 2008/0038261 A1 | 2/2008 | Grillo-Lopez |
| 2009/0074760 A1 | 3/2009 | Grillo-Lopez et al. |

FOREIGN PATENT DOCUMENTS

| | | |
|---|---|---|
| EP | 0 274 394 A2 | 7/1988 |
| EP | 0 510 949 A2 | 4/1991 |
| EP | 0 125 023 A1 | 11/1994 |
| EP | 0 682 040 A1 | 11/1995 |
| EP | 0 451 216 B1 | 1/1996 |
| EP | 0 669 836 B1 | 3/1996 |
| EP | 0 752 248 A1 | 1/1997 |
| EP | 1616572 B1 | 9/2010 |
| WO | 87/02671 A1 | 5/1987 |
| WO | 88/04936 A1 | 7/1988 |
| WO | 89/00999 A1 | 2/1989 |
| WO | 91/04320 A1 | 4/1991 |
| WO | 92/07466 A1 | 5/1992 |
| WO | 93/02108 A1 | 2/1993 |
| WO | 94/08601 | 4/1994 |
| WO | 94/11026 A2 | 5/1994 |
| WO | 96/32107 | 10/1996 |
| WO | 97/05870 | 2/1997 |
| WO | 97/05873 | 2/1997 |
| WO | 98/42378 | 10/1998 |
| WO | 00/09160 A1 | 2/2000 |
| WO | 00/27428 A1 | 5/2000 |
| WO | 00/27433 A1 | 5/2000 |
| WO | 01/10460 A1 | 2/2001 |
| WO | 2004/056312 A2 | 7/2004 |

OTHER PUBLICATIONS

Alas S. et al. *Clin. Cancer Res.* 8(3): 836-45, 2002. Rituximab modifies the cisplatin-mitochondrial signaling pathway, resulting in apoptosis in cisplatin-resistant non-Hodgkin's lymphoma.

Almasri N. M. et al. *Am. J. Hematol.* 40: 259-63, 1992. Reduced expression of CD20 antigen as a characteristic marker for chronic lymphocytic leukemia.

Anderson D.R. et al. *Biochem. Soc. Trans.* 25(2): 705-08, 1997. Targeted anti-cancer therapy using rituximab, a chimaeric anti-CD20 antibody (IDEC-C2B8) in the treatment of non-Hodgkin's B-cell lymphoma.

Anderson. D.R. et al. Second IBC Int'l. Conference on Antibody Engineering, San Diego, Dec. 16-18, 1991. Immunoreactivity and effector function associated with a chimeric anti-CD20 antibody (abstract of presentation).

Anderson K.C. et al. *Blood* 63(6): 1424-33, 1984. Expression of human B cell-associated antigens on leukemias and lymphomas: a model of human B cell differentiation.

Anderson K.C. et al. *Blood* 69(2): 597-604, 1987. Hematologic engraftment and immune reconstitution posttransplantation with anti-B1 purged autologous bone marrow.

Appelbaum F.R. *Hem. One. Clin. N. Amer.* 5(5): 1013-25, 1991. Radiolabeled monoclonal antibodies in the treatment of non-Hodgkin's lymphoma.

Armitage J.O. et al. *Cancer* 50: 1695-1702, 1982. Predicting therapeutic outcome in patients with diffuse histiocytic lymphoma treated with cyclophosphamide, adriamycin, vincristine and prednisone (CHOP).

Armitage J.O. et al. *J. Clin. Oncol.* 16(8): 2780-95, 1998. New approach to classifying non-Hodgkin's lymphomas: clinical features of the major histologic subtypes. Non-Hodgkin's Lymphoma Classification Project.

Arranz R. et al. *J. Clin. Oncol.* 16(4): 1538-46, 1998. Role of interferon alfa-2b in the induction and maintenance treatment of low-grade non-Hodgkin's lymphoma: results from a prospective, multicenter trial with double randomization.

Attachment from The Second Annual IBC International Conference on Antibody Engineering, Dec. 16-18, 1991. San Diego, CA (abstract only).

Azogui O. et al. *J. Immunol.* 131: 1205-08, 1983. Inhibition of IL-2 production after human allogeneic bone marrow transplantation.

Badger C.C. et al. *Cancer Res.* 46: 6223-28, 1986. Experimental radioimmunotherapy of murine lymphoma with $^{131}$I-labeled anti-T-cell antibodies.

Belhadj K. et al. *Ann. Oncol.* 15: 504-10, 2004. Efficiency of in vivo purging with rituximab prior to autologous peripheral blood progenitor cell transplantation in B-cell non-Hodgkin's lymphoma: a single institution study.

Berinstein N. et al. *Proc. Amer. Assn. Cancer Res.* 38: 85, abst. No. 567, Mar. 1997. IDEC-C2B8 (rituximab) levels correlate with response in low-grade or follicular non-Hodgkin's lymphoma (LG-F-NHL).

Berinstein N.L. et al. *Ann. Oncol.* 9: 995-1001, 1998. Association of serum rituximab (IDEC-C2B8) concentration and anti-tumor response in the treatment of recurrent low-grade or follicular non-Hodgkin's lymphoma.

Berne et al. (eds.), Principles of Physiology, CV Mosby Co., St. Louis, p. 190 (1990).

Beychok S. (in) *Cells of Immunoglobulin Synthesis*, B. Pernis et al., eds. New York: Academic Press, 1979, 69-88. Comparative aspects of in vitro and cellular assembly of immunoglobulins.

Bhan A.K. et al. *J Exp. Med.* 154: 737-49, 1981. Stages of B cell differentiation in human lymphoid tissue.

Bierman P.J. et al. (in) Hoffman, R., ed., *Hematology*, 2d. ed. (Churchill Livingstone), 1995. Chapter 81, pp. 1278-1298. Clinical manifestations and staging of and therapy for non-Hodgkin's lymphomas.

*Biogen Idec Inc.* v. *Corixa Corp.*, Case No. 01-CV-1637 IEG (RBB), Order Granting Patentees' Motion for Reconsideration, etc. (S.D. Cal., Jan. 22, 2004).

*Biogen Idec Inc.* v. *Corixa Corp.*, Case No. 01-CV-1637 IEG (RBB), Stipulation of Dismissal of Claims and Counterclaims with Prejudice and Order (S.D.Cal., May 13, 2004).

Bosly A. et al. *Nouv. Rev. Fr. Hematol.* 32(1): 13-16, 1990. Interleukin-2 after autologous bone marrow transplantation as consolidative immunotherapy against minimal residual disease.

Boulianne G.L. et al. *Nature* 312: 643-46, 1984. Production of functional chimaeric mouse/human antibody.

Brunner K.T. et al. *Immunology* 14(2): 181-96, 1968. Quantitative assay of the lytic action of immune lymphoid cells on $^{51}$Cr-labelled allogeneic target cells in vitro; inhibition by isoantibody and by drugs.

Buchsbaum D.J. et al. *Cancer Res.* 50: 993s-999s, 1990. Comparative binding and preclinical localization and therapy studies with radiolabeled human chimeric and murine 17-1A monoclonal antibodies.

Buchsbaum D.J. et al. *Cancer Res.* 52: 637-642, 1992. Improved delivery of radiolabeled anti-B1 monoclonal antibody to Raji lymphoma xenografts by predosing with unlabeled anti-B1 monoclonal antibody.

Buchsbaum D.J. et al. Cancer Res. 52: 6476-81, 1992. Therapy with unlabeled and $^{131}$I-labeled pan-B-cell monoclonal antibodies in nude mice bearing Raji Burkitt's lymphoma xenografts.

Buchsbaum D.J. et al. *I.J. Rad. Oncol. Biol. Phys.* 18: 1033-41, 1990. A comparison of $^{131}$I-labeled monoclonal antibody 17-1A treatment to external beam irradiation on the growth of LS174T human colon carcinoma xenografts.

Buchsbaum D.J. et al. *I.J. Rad. Oncol. Biol. Phys.* 25(4): 629-38, 1993. Comparison of $^{131}$I- and $^{90}$Y-labeled monoclonal antibody 17-1A for treatment of human colon cancer xenografts.

Byrd J.C. *Genentech Onlcology and IDEC Pharmaceuticals Investigator Initiated Protocol Concept Worksheet*, 1998. Phase I Study of Thrice Weekly Administration of IDEC-C2B8 in Patients with Chronic Lymphocytic Leukemia (CLL) Small Lymphocytic Lymphoma (SLL).

Byrd J.C. et al. *Blood* 92(10 Suppl. 1): 106a, abst. No. 432, Nov. 1998. Rituximab therapy in hematologic malignancy patients with circulating blood tumor cells: association with increased infusion-related side effects and rapid tumor lysis.

Byrd J.C. et al. *Blood* 92(10 Suppl. 1): 106a, abst. No. 433, Nov. 1998. Rituximab therapy in previously treated Waldenstrom's macroglobulinemia: preliminary evidence of activity.

Byrd J.C. *Cancer Blather. Radiopharm.* 14(4)L 323, 1999. Rituximab therapy in patients with chronic lymphocytic leukemia.

Byrd et al. *J. Clin. Oncol.* 17(3): 791-795, Mar. 1999. Rituximab therapy in hematologic malignancy patients with circulating blood tumor cells: association with increased infusion-related side effects and rapid blood tumor clearance.

Byrd J.C. et al. *J. Clin. Oncol.* 19(8): 2153-64, 2001. Rituximab using a thrice weekly dosing schedule in B-cell chronic lymphocytic leukemia and small lymphocytic lymphoma demonstrates clinical activity and acceptable toxicity.

Caligiuri M.A. *Semin. Oncol.* 20(6 Suppl 9): 3-10, 1993. Low-dose interleukin-2 therapy: rationale and potential clinical applications.

Caligiuri M.A. et al. *J. Clin. Oncol.* 9(12): 2110-19, 1991. Extended continuous infusion low-dose recombinant interleukin-2 in advanced cancer: prolonged immunomodulation without significant toxicity.

Caligiuri M.A. et al. *J. Clin. Invest.* 91(1): 123-32, 1993. Selective modulation of human natural killer cells in vivo after prolonged infusion of low dose recombinant interleukin 2.

Calvert J.E. et al. *Semin. Hematol.* 21(4): 226-243, 1984. Cellular events in the differentiation of antibody-secreting cells.

Carrasquillo J.A. et al. *J. Nucl. Med.* 26: 67, abst. No. 276, 1985. Improved imaging of metastatic melanoma with high dose 9.2.27 In-111 monoclonal antibody.

Catovsky D. et al. *Eur I Cancer* 31A(13/14): 2146-54 (1995). Key issues in the treatment of chronic lymphocytic leukaemia (CLL).

Cayeux S. et al. *Blood* 74(6): 2270-77, 1989. T-cell ontogeny after autologous bone marrow transplantation: failure to synthesize interleukin-2 (IL-2) and lack of CD2- and CD3-mediated proliferation by both CD4- and CD8+ cells even in the presence of exogenous IL-2.

Chen J.J. et al. *J. Immunol.* 143(3): 1053-57, 1989. Tumor idiotype vaccines. VI. Synergistic anti-tumor effects with combined "internal image" anti-idiotypes and chemotherapy.

Cheson B.D. et al. *Blood* 87: 4990-97, 1996. National Cancer Institute-specified working group guidelines for chronic lymphocytic leukemia: revised guidelines for diagnosis and treatment.

Chinn P. et al. *Proc. Ann. Mtg. Am. Assn. Cancer Res.* 33: 337, abst. No. 2012, 1992. Production and characterization of radiolabeled anti-CD20 monoclonal antibody: potential application to treatment of B-cell lymphoma.

Chinn P.C. et al. *Int. J. Oncol.* 15(5): 1017-25, Nov. 1999. Preclinical evaluation of 90Y-labeled anti-CD20 monoclonal antibody for treatment of non-Hodgkin's lymphoma.

Chinn P.C. et al. *Proc. Ann. Mtg. Am Assn. Cancer Res.* 40: 574, abst. No. 3786, 1999. A $^{90}$Y-labeled anti-CD20 monoclonal antibody conjugated to MX-DTPA, a high-affinity chelator for yttrium.

Chomczynki P. et al. *Anal. Biochem.* 162: 156-59, 1987. Single-step method of RNA isolation by acid guanidinium thiocyanate-phenol-chloroform extraction.

Chow K.U. et al. *Haematologica* 87: 33-43, 2002. Anti-CD20 antibody (IDEC-C2B8, rituximab) enhances efficacy of cytotoxic drugs on neoplastic lymphocytes in vitro: role of cytokines, complement, and caspases.

Clark E.A. et al. *J. Cell. Biochem.* (Suppl. 9A): 63, 1985. Anti-Bp35 antibody induces human B cell proliferation: implications for in vivo immunotherapy.

Clark E.A. et al. *Proc. Natl. Acad. Sci. USA* 82(6): 1766-70, 1985. Role of the Bp35 cell surface polypeptide in human B-cell activation.

Classon B.J. et al. *J. Exp. Med.* 169(4): 1497-1502, 1989. The primary structure of the human leukocyte antigen CD37, a species homologue of the rat MRC OC-44 antigen.

Cogliatti S.B. et al. *Sw. Med. Weekly* 192: 607-17, 2002. Who is *WHO* and what was *REAL*?

Cohen Y. et al. *Leuk. Lymphoma* 43(7): 1485-87, 2002. Large B-cell lymphoma manifesting as an invasive cardiac mass: sustained local remission after combination of methotrexate and rituximab.

Coiffier B. et al. *Blood* 92(6): 1927-32, 1998. Rituximab (anti-CD20 monoclonal antibody) for the treatment of patients with relapsing or refractory aggressive lymphoma: a multicenter phase II study.

Coiffier B. et al. *N. Engl. J. Med.* 346(4): 235-42, 2002. CHOP chemotherapy plus rituximab compared with CHOP alone in elderly patients with diffuse large-B-cell lymphoma.

Coiffier B. *Ann. Oncol.* 83(Suppl 1): S73-S74, 2004. New treatment strategies in lymphomas: aggressive lymphomas.

Coleman M. et al. *Blood* 102(11 pt.1): 29a, abst. No. 29, 2003. The Bexxar® therapeutic regimen (tositumomab and Iodine I-131 tositumomab) produced durable complete remissions in heavily pretreated patients with non-Hodgkin's lymphoma (NHL), rituximab-relapsed/ refractory disease, and rituximab-naive disease.

Colombat P. et al. *Blood* 97: 101-06, 2001. Rituximab (anti-CD20 monoclonal antibody) as single first-line therapy for patients with follicular lymphoma with a low tumor burden: clinical and molecular evaluation.

Cope, *Oncology* 8(4): 100, 1994. Antibody shows promise in treating B-cell lymphoma.

Curti B.D. *Crit. Rev. Oncol. Hematol.* 14(1): 29-39, Feb. 1993. Physical barriers to drug delivery in tumors.

Czuczman M. et al. *Blood* 94(10 Supp. 1): 99a, abst. No. 432, 1999. Rituximab/CHOP chemoimmunotherapy in patients (PTS) with low grade lymphoma (LG/F NHL): progression free survival (PFS) after three years (median) follow-up.

Czuczman M.S. et al. *J. Clin. Oncol.* 17(1): 268-76, Jan. 1999. Treatment of patients with low-grade B-cell lymphoma with the combination of chimeric anti-CD20 monoclonal antibody and CHOP chemotherapy.

Davis T. et al. *Blood* 90(10 Suppl. 1): 509a, abst No. 2269 (Nov. 1997). Retreatments with RITUXAN™ (Rituximab, Idec-C2B8) have significant efficacy, do not cause HAMA, and are a viable minimally toxic alternative in relapsed or refractory non-Hodgkin's lymphoma (NHL).

Davis T. et al.. *Proc. Ann. Mtg. ASCO* 17: abst. No. 39 (May 1998). Combination immunotherapy of low grade or follicular (LG/F) non-Hodgkin's lymphoma (NHL) with rituximab and alpha interferon: interim analysis.

Davis T.A. et al. *Blood* 86(10 Suppl. 1): 237a, abst. No. 1080, 1995. $^{90}$Yttrium labeled anti-CD20 therapy for recurrent B cell lymphoma.

Davis T.A. et al. *Blood* 92(10 Suppl. 1): 414a, abst. No. 1710, Nov. 1998. Rituximab: phase II (PII) retreatment (ReRx) study in patients (PTS) with low grade or follicular (LG/F) NHL.

Davis T.A. et al. *Blood* 92(10 Suppl. 1): 414a, abst. No. 1711, Nov. 1998. Rituximab: first report of a phase II (PII) trial in NHL patients (PTS) with bulky disease.

Davis T.A. et al. *Clin. Cancer Res.* 5(3): 611-15, 1999. Therapy of B-cell lymphoma with anti-CD20 antibodies can result in the loss of CD20 antigen expression.

Davis T.A. et al. *J. Clin. Oncol.* 17(6): 1851-57, 1999. Single-agent monoclonal antibody efficacy in bulky non-Hodgkin's lymphoma: results of a phase Ii trial of rituximab.

Davis T.A. et al. *Proc. Ann. Mtg. Amer. Assn. Cancer Res.* 39: 435, abst. No. 2964, 1998. Therapy of B cell lymphoma with anti-CD20 can result in relapse with loss of CD20 expression.

Definition of "white blood cell" from the Online Medical Dictionary, available at http://cancerweb.ncl.ac.uk, accessed Nov. 13, 1997.

Definition of "white blood cell count" from MedTerms (the Medical Dictionary of MedicineNet.com), available at http://www.medterms.com, accessed Jul. 25, 2001.

Demidem A. et al. *Cancer Biother. Radiopharm.* 12(3): 177-86, 1997. Chimeric anti-CD20 (IDEC-C2B8) monoclonal antibody sensitizes a B cell lymphoma cell line to cell killing by cytotoxic drugs.

DeNardo G.L. et al. *Cancer Res.* 50(3 Suppl.): 1014s-1016s, 1990. Fractionated radioimmunotherapy of B-cell malignancies with $^{131}$I-Lym-1.

DeNardo G.L. et al. *I.J. Rad. Oncol. Biol. Phys.* 11(2): 335-48, 1985. Requirements for a treatment plan in system for radioimmunotherapy.

DeNardo S.J. et al. *Antibody Immunoconj. Radiopharm.* 1(1): 17-33, 1988. Pilot studies of radioimmunotherapy of B cell lymphoma and leukemia using 1-131 Lym-1 monoclonal antibody.

DeNardo S.J. et al. *Cancer* 73(3 Suppl.): 1023-32, 1994. The biologic window for chimeric L6 radioimmunotherapy.

Di Gaetano N. et al. *Br. J. Haematol.* 114(4): 800-09, 2001. Synergism between fludarabine and rituximab revealed in a follicular lymphoma cell line resistant to the cytotoxic activity of either drug alone.

Dickson S. *Gen. Engr. News* 5(3): 1, Mar. 1985. Scientists produce chimeric monoclonal Abs.

Dillman R.O. *J. Clin. Oncol.* 12(7): 1497-1515, 1994. Antibodies as cytotoxic therapy.

Eary J.F. et al. *J. Nuc. Med.* 31(8): 1257-68, 1990. Imaging and treatment of B-cell lymphoma.

Einfeld D.A. et al. *EMBO J.* 7: 711-17, 1988. Molecular cloning of the human B cell CD20 receptor predicts a hydrophobic protein with multiple transmembrane domains.

Eisenbeis C.F. et al. *Clin. Cancer Res.* 10: 6101-10 (2004). Combination immunotherapy of B-cell cell non-Hodgkin's lymphoma with rituximab and interleukin-2: a preclinical and phase I study.

Endo K. *Jpn. J. Cancer Chemother.* 26: 744-48, 1999. Current status of nuclear medicine in Japan.

Engert A. et al. *Ann. Hematol.* 77(suppl. 2): S180, abst. No. 717. Multicenter phase II study of the monoclonal anti-CD20 antibody rituximab (IDEC-C2B8) in patients with intermediate/high grade non-Hodgkin's lymphoma, 1998.

Fisher et al. *Blood* 92:247a. 1998. Phase 1 Trial with CD40-activated Follicular Lymphoma Cells: A Novel Cellular Vaccine Strategy for B Cell Malignancies [abstract].

Flinn I.W. et al. *Blood* 92(10 Suppl. 1): 648a, abst. No. 2678, Nov. 1998. In vivo purging and adjuvant immunotherapy with rituximab during PBSC transplant for NHM [sic].

Foran J.M. et al. *Br. J. Haematol.* 102(1): 149, 1998. Immunotherapy of mantle cell lymphoma (MCL), lymphoplasmacytoid lymphoma (LPC) and Waldentrom's macroglobulinemia (WM), and small lymphocytic leukemia (SLL) with rituximab (IDEC-C2B8): preliminary results of an ongoing international multicentre trial.

Foran J.M. et al. *J. Clin. Oncol.* 18: 317-24, 2000. European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma.

Ford et al. *Highlights in Oncology Practice* 16(2): 40-50, 1998. Immunotherapeutic approaches to treatment of B-cell neoplasms: focus on unconjugated antibodies.

Fox, Human Physiology, Wm. C. Brown Publishers, Dubuque, Iowa, p. 366 (1984).

Freedman A.S. et al. *Blood* 70(2): 418-427, 1987. Normal Cellular Counterparts of B Cell Chronic Lymphocytic Leukemia.

Freedman A.S. et al. *J. Clin. Oncol.* 8: 784-91, 1990. Autologous bone marrow transplantation in B-cell non-Hodgkin's lymphoma: very low treatment-related mortality in 100 patients in sensitive relapse.

Fridik M.A. et al. *Ann. Hematol.* 74(1): 7-10, 1997. First-line treatment of Waldenström's disease with cladribine.

Friedberg J.W. et al. *Expert Rev. Anticancer Ther.* 4(1): 18-26, 2004. Iodine-131 tositumomab (Bexxar®): radioimmunoconjugate therapy for indolent and transformed B-cell non-Hodgkin's lymphoma.

Ga et al., "Use of rituximab, the new FDA-approved antibody," Curr. Opin. Oncol. 10(6): 548-51 (Nov. 1998). (abstract only).

Gianni A.M. et al. *Blood* 102: 749-55, 2003. Long-term remission in mantle cell lymphoma following high-dose sequential chemotherapy and in vivo rituximab-purged stem cell autografting (R-HDS regimen).

Ginaldi L. et al. *J. Clin. Pathol.* 51: 364-69, 1998. Levels of expression of CD19 and CD20 in chronic B leukaemias.

Golay J.T. et al. *J. Immunol.* 135(6): 3795-801, 1985. The CD20 (Bp35) antigen is involved in activation of B cells from the G0 to the G1 phase of the cell cycle.

Golay J. et al. *Haematologica* 88: 1002-12, 2003. Rituximab-mediated antibody-dependent cellular cytotoxicity against neoplastic B cells is stimulated strongly by interleukin-2.

Goldenberg D.M. et al. *J. Clin. Oncol.* 9(4): 548-64, 1991. Imaging and therapy of gastrointestinal cancers with radiolabeled antibodies.

Gordon L.I. et al. *Blood* 94(10 Suppl. 1): 91a, abst. No. 396, 1999. ZEVALIN™ (IDEC-Y2B8) radioimmunotherapy of rituximab refractory follicular non-Hodgkin's lymphoma (NHL): interim results.

Gordon L.I. et al. *J. Immunother.* 22(5): 459, 1999. Update on IDEC-Y2B8 (Zevalin™) radioimmunotherapy of B-cell NHL.

Greenberger J.S. et al. *Cancer Res.* 45(2): 758-67, 1985. Effects of monoclonal antibody and complement treatment of human marrow on hematopoiesis in continuous bone marrow culture.

Greiner J.W. et al. *Science* 235(4791): 895-98, 1987. Recombinant interferon enhances monoclonal antibody-targeting of carcinoma lesions in vivo.

Gribben J.G. et al. *N. Engl. J. Med.* 325(22): 1525-32, 1991. Immunologic purging of marrow assessed by PCR before autologous bone marrow transplantation for B-cell lymphoma.

Grillo-López A.J. IBC Int'l. Conference on Antibody Engineering, La Jolla, Dec. 1994, IDEC-C2B8 chimeric antibody and IDEC-Y2B8 radiolabeled antibody phase I and II studies in patients with non-Hodgkin's lymphoma (abstract of presentation).

Grillo-López A.J. et al. *Ann. Oncol.* 7(3 Suppl.): 57, abst. No. 195, 1996. Treatment (rx) of relapsed non-Hodgkin's lymphoma (NHL) using the 90-yttrium (90-Y) labeled anti-CD20 monoclonal antibody (MAB) IDEC-Y2B8: a phase I clinical trial (PI CT).

Grillo-López A.J. et al. *Antibody Immunoconj. Radiopharm.* 8: 60, abst. no. 10, 1995. Treatment options for patients with relapsed low-grade or follicular lymphoma: the role of IDEC-C2B8.

Grillo-López A.J. et al. *Blood* 86(10 Suppl. 1): 55a, abst. No. 207, 1995. Phase 1 study of IDEC-Y2B8: 90-yttrium labeled anti-CD20 monoclonal antibody therapy of relapsed non-Hodgkin's lymphoma.

Grillo-López A.J. et al. *Br. J. Haematol.* 93(Suppl. 2): 283, abst. No. 1072, 1996. IDEC-C2B8 chimeric anti-CD20 antibody (MAB): safety and clinical activity in the treatment of patients (PTS) with relapsed low-grade or follicular (IWF:A-D) non-Hodgkin's lymphoma (NHL).

Grossbard M.L. et al. *Blood* 80(4): 863-78, 1992. Monoclonal antibody-based therapies of leukemia and lymphoma.

Gura T. *Science* 278: 1041-42, 1997. Systems for identifying new drugs are often faulty.

Guyton, "Resistance of the body to infection—the leukocytes, the macrophage system, and inflamation," Textbook of Medical Physiology, 7th ed., WB Saunders Co., Philadelphia, p. 51 (1986).

Hagenbeek A. et al. *J. Clin. Oncol.* 16(1): 41-47, 1998. Maintenance of remission with human recombinant interferon alfa-2a in patients with stages III and IV low-grade malignant non-Hodgkin's lymphoma. European Organization for Research and Treatment of Cancer Lymphoma Cooperative Group.

Hainsworth J.D. et al. *Blood* 95: 3052-56, 2000. Rituximab monoclonal antibody as initial systemic therapy for patients with low-grade non-Hodgkin lymphoma.

Harris N.L. et al. *Blood* 54(5): 1361-92, 1994. A revised European-American classification of lymphoid neoplasms: a proposal from the International Lymphoma Study Group.

Harris N.L. et al. *J. Clin. Oncol.* 17(12): 3835-49, 1999. World Health Organization classification of neoplastic diseases of the hematopoietic and lymphoid tissues: report of the Clinical Advisory Committee meeting—Airlie House, Virginia, Nov. 1997.

Hartwell L.H. et al. *Science* 278: 1064-68, 1997. Integrating genetic approaches into the discovery of anticancer drugs.

Hekman A. et al. *Ann. Rept. Netherlands Cancer Inst.*, Amsterdam, pp. 47-48, 1993. Immunotherapy.

Herold M. et al. *Ann. Hematol.* 79: 332-335, 2000. Successful treatment and re-treatment of resistant B-cell chronic lymphocytic leukemia with the monoclonal anti-CD20 antibody rituximab.

Hiddemann W. et al. *Blood* 88(11): 4085-89, 1996. Lymphoma classification—the gap between biology and clinical management is closing.

Hillmen P. et al. *Semin. Oncol.* 31(1 suppl. 2): 22-26, 2004. Advancing therapy for chronic lymphocytic leukemia—the role of rituximab.

Hooijberg E. et al. *Cancer Res.* 55: 2627-34, 1995. Eradication of large human B cell tumors in nude mice with unconjugated CD20 monoclonal antibodies and interleukin 2.

Horning S.J. et al. *Blood* 100(11 part 1): 357a, abst. No. 1385, 2002. Rituximab treatment failures: tositumomab and Iodine 1131 tositumomab (Bexxar®) can produce meaningful durable responses.
IDEC Pharmaceuticals Corp., U.S. Securities and Exchange Commission Form S-1 Registration Statement, 1991.
IDEC Pharmaceuticals Corp., press release dated Dec. 9, 1996. IDEC Pharmaceuticals and Genentech announce positive final results for pivotal phase III trial of IDEC-C2B8 as single agent.
IDEC Pharmaceuticals Corp. and Genentech, Inc., Product insert for Rituxan® approved by U.S. Food and Drug Administration on Nov. 26, 1997.
*IDEC Pharmaceuticals Corp v. Corixa Corp.* Case No. 01-1637-IEG [Doc. Nos. 486, 584] (S.D. Cal. Oct. 14, 2003.
Imrie, K. et al. *Curr. Oncol.* 6(4): 228-35, 1999. Use of rituximab in the treatment of lymphoma: an evidence summary.
International Non-Hodgkin's Lymphoma Prognostic Factors Project. *N. Engl. J. Med.* 329(14): 987-94, 1993. A predictive model for aggressive non-Hodgkin's lymphoma.
Jain R.K. *Sci. Am.* 271(1): 58-65, 1994. Barriers to drug delivery in solid tumors.
Janakirman N. et al. *Blood* 92(10 Suppl. 1): 337a, abst. No. 1384, Nov. 1998. Rituximab: correlation between effector cells and clinical activity in NHL.
Jazirehi A.R. et al. *Oncogene* 24: 2121-43, 2005. Cellular and molecular signal transduction pathways modulated by rituximab (rituxan, anti-CD20 mAb) in non-Hodgkin's lymphoma: implications in chemosensitization and therapeutic intervention.
Jensen,e t al. *Ann. Hematol.* 77:89-91. 1998. Rapid tumor lysis in a patient with B-cell chronic lymphocytic leukemia and lymphocytosis treated with an anti-CD20 monoclonal antibody (IDEC-C2B8, rituximab).
Juweid M. et al. *Cancer Res.* 55(23 Suppl.): 5827s-5831s, 1995. Estimates of red marrow dose by sacral scintigraphy in radioimmunotherapy patients having non-Hodgkin's lymphoma and diffuse bone marrow uptake.
Juweid M. et al. *Cancer Res.* 55(23 Suppl.): 5899s-5907s, 1995. Treatment of non-Hodgkin's lymphoma with radiolabeled murine, chimeric, or humanized LL2, an anti-CD22 monoclonal antibody.
Kaminski M. et al. *Antibody Immunoconj. Radiopharm.* 4(1): 36, abst. No. 66, 1991. Phase I trial results of 131-1 antibody radioimmunotherapy (RAIT) of B-cell lymphoma.
Kaminski M.S. et al. *Antibody Immunoconj. Radiopharm.* 5(3): 345, abst. No. 57, 1992. Initial clinical radioimmunotherapy results with $^{131}$I-anti-B1 (anti-CD20) in refractory B-cell lymphoma.
Kaminski M.S. et al. *Blood* 76(10 Suppl. 1): 355a, abst. No. 1409, 1990. Phase I evaluation of 131-1 MB-1 antibody radioimmunotherapy (RIT) of B-cell lymphoma.
Kaminski M.S. et al. *Blood* 78(10 Suppl. 1): 43a, abst. No. 161, 1992. Radioimmunotherapy (RIT) of refractory B-cell lymphoma with 131-I-anti-B1 (anti-CD20) antibody: promising early results using non-marrow ablative radiation doses.
Kaminski M.S. et al. *J Clin. Oncol.* 14(7): 1974-81, 1996. Iodine-131-anti-B1 radioimmunotherapy for B-cell lymphoma.
Kaminski M.S. et al. *N. Engl. J. Med.* 329: 459-65, 1993. Radioimmunotherapy of B-cell lymphoma with [$^{131}$I]anti-B1 (anti-CD20) antibody.
Kaminski M. et al. Proc. Third Conf. on Radioimmunodetection and Radioimmunotherapy of Cancer, Princeton NJ, Nov. 15-17, 1990 (published at *Antibody Immunoconj. Radiopharm.* 4: 387, 1991), abst. No. 144. 131-I anti-B1: Initial clinical evaluation in B-cell lymphoma.
Kaminski M. et al. *Antibody Immunoconj. Radiopharm.* 4(1): 36, abst. No. 66, 1991. Phase I trial results of 131-I antibody radioimmunotherapy (RAIT) of B-cell lymphoma.
Kaminski M. et al, *Antibody Immunoconj. Radiopharm.* 3(1): abst. No. 83, 1990. Radioimmunotherapy of advanced B-cell lymphoma with non bone marrow ablative doses of 131-I MB-1 antibody.
Kaminski M. et al. *Proc. Amer. Soc. Clin. Oncol.* 9: 271, abst. No. 1051, 1990. Radioimmunodetection (RID) and non marrow ablative radioimmunotherapy (RIT) of B-cell lymphoma with 131-I MB-1 antibody.

Kaminski M. et al. *J. Clin. Oncol.* 10(11): 1696-1711, 1992. Imaging, dosimetry, and radioimmunotherapy with iodine 131-labeled anti-CD37 antibody in B-cell lymphoma.
Keating M. et al. *Semin. Oncol.* 27(6 suppl. 12): 86-90, 2000. High-dose rituximab therapy in chronic lymphocytic leukemia.
Kinoshita T. et al. *J. Clin. Oncol.* 16(12): 3916, Dec. 1998. CD20-negative relapse in B-cell lymphoma after treatment with Rituximab.
Klarnet J.P. et al. *J. Immunol.* 138(11): 4012-17, 1987. Antigen-driven T cell clones can proliferate in vivo, eradicate disseminated leukemia, and provide specific immunologic memory.
Knox S.J. et al. *Clin. Cancer Res.* 2: 457-70, 1996. Yttrium-90-labeled anti-CD20 monoclonal antibody therapy of recurrent B-cell lymphoma.
Knox S.J. et al. *I.J. Rad. Oncol. Biol. Phys.* 32: 215, 1995. $^{90}$Y-anti-CD20 monoclonal antibody therapy for recurrent B cell lymphoma.
Knox S.J. et al. *J. Immunother.* 16(2): 161, abst. No. 51, 1994. $^{90}$Y-anti-CD20 monoclonal antibody therapy (IDEC-Y2B8) for recurrent B cell lymphoma.
Ku et al., "Influence of various cytokines on the expression of CD20 on the surface of CLL-cells in vitro," Leuk . Res. 25(1): 99-100 (Jan. 2001).
Kuzel T. et al. *Cancer Biother.* 8(1): 3-16, 1993. A phase I escalating-dose safety, dosimetry and efficacy study of radiolabeled monoclonal antibody LYM-1.
Langmuir V.K. *Nucl. Med. Biol.* 19(2): 213-55, 1992. Radioimmunotherapy: clinical results and dosimetric considerations.
Larson S.M. et al. *Nucl. Med. Biol.* 16: 153-58, 1989. Comparison of bone marrow dosimetry and toxic effect of high dose *131*I-labeled monoclonal antibodies administered to man.
Lauria F. et al. *Bone Marrow Transplant.* 18(1): 79-85, 1996. Immunologic and clinical modifications following low-dose subcutaneous administration of rIL-2 in non-Hodgkin's lymphoma patients after autologous bone marrow transplantation.
Leichner P.K. et al. *Front. Rad. Ther. Oncol.* 24: 109-20, 1990. Dosimetry and treatment planning in radioimmunotherapy.
Leichner P.K. et al. *Med. Phys.* 20(2): 529-34, 1993. Tumor dosimetry in radioimmunotherapy: methods of calculation for beta particles.
Levy R. et al. *Fed. Proc.* 42: 2650-56, 1983. Tumor therapy with monoclonal antibodies.
Ling N.R. et al. (in) *Leucocyte Typing III: White Cell Differentiation Antigens*, A.J. McMichael et al., eds., Oxford: Oxford Univ. Pr., 1987, pp. 302-335. B-cell and plasma cell antigens: new and previously defined clusters.
Link B.K. et al. *Proc. Ann. Mtg. ASCO* 17: 3a, abst. No. 7, 1998. Phase II pilot study of the safety and efficacy of rituximab in combination with CHOP chemotherapy in patients with previously untreated intermediate- or high-grade NHL.
Link M.P. et al. *J. Immunol.* 137(9): 3013-18, 1986. A unique antigen on mature B-cells defined by a monoclonal antibody.
Lipton J.M. et al. *Blood* 60(5 Suppl. 1): 170a, abst. No. 609, 1992. Distribution of B1, CALLA, β2 microglobulin and Ia on hematopoiesis supporting cells (HSC) in short and long-term cultures.
Liu A.Y. et al. *J. Immunol.* 139(10): 3521-3526, Nov. 15, 1987. Production of a mouse-human chimeric monoclonal antibody to CD20 with potent fc-defendant biologic activity.
Lonberg N. et al. *Nature* 368: 856-59, 1994. Antigen-specific human antibodies from mice comprising four distinct genetic modifications.
Lorigan et al., "Tumour lysis syndrome, case report and review of the literature," Ann. Oncol. 7(6): 631-36 (Aug. 1996).
Lowman H.B. Slides presented at IBC Antibody Engineering Conference, Dec. 2, 2003. Differential activities in a series of humanized anti-CD20 antibodies.
Lum L.G. et al. *Blood* 69(2): 369-80, 1987. The kinetics of immune reconstitution after human marrow transplantation.
Macey D.J. et al. *Front. Rad. Ther. Oncol.* 24: 123-31, 1990. A treatment planning program for radioimmunotherapy.
Macklis R.M. et al. *Antibody Immunoconj. Radiother.* 5(3): asbst. No. 39, 1992. Induction of programmed cell death in malignant lymphomas after radioimmunotherapy.
Macklis R.M. et al. *Cancer* 73(3 Suppl.): 966-73, 1994. Radiobiologic studies of low-dose-rate $^{90}$Y-lymphoma therapy.

Maddy A.H. et al. *Immunol.* 68(3): 346-52, 1989. The role of cell maturation in the generation of phenotypic heterogeneity in B-cell chronic lymphocytic leukaemia.

Maloney D.G. et al. *Blood* 80(6): 1502-1510, 1992. Monoclonal anti-idiotype antibody therapy of B-cell lymphoma: the addition of a short course of chemotherapy does not interfere with the antitumor effect nor prevent the emergence of idiotype-negative variant cells.

Maloney D.G. et al. *Blood* 88(10: Suppl. 1): 637a, abst. No. 2635, 1996. The anti-tumor effect of monoclonal anti-CD20 antibody (mAb) therapy includes direct anti-proliferative activity and induction of apoptosis in CD20 positive non-Hodgkin's lymphoma (NHL) cell lines.

Maloney D.M. et al. *Blood* 84(8): 2457-66, 1994. Phase I clinical trial using escalating single-dose infusion of chimeric anti-CD20 monoclonal antibody (IDEC-C2B8) in patients with recurrent B-cell lymphoma.

Maloney et al. *Blood* 90(6):2188-2195. Sep. 15, 1997. IdDEC-C2B8 (Rituximab anti-CD20 monoclonal antibody therapy in patients with relapsed low-grade non-Hodgkin's lymphoma.

Maloney et al. *J. Clin. Oncol.* 15(10):3266-3274, Oct. 1997. IDEC-C2B8: Results of a phase I multiple-dose trial in patients with relapsed non-hodgkin's lymphoma.

Mariuzza et al. *Science.* 233: 747-53, 1986. Three-dimensional structure of an antigen-antibody complex at 2.8 Å resolution.

Marquez S.D. et al. *I.J. Rad. Oncol. Biol. Phys.* 39: 327, abst. No. 2173, 1997. Hematological toxicity in radioimmunotherapy is predicted both by the computed absorbed whole body dose (cGy) and by the administered dose (mCi).

Marti G.E. et al. *Ann. N.Y. Acad. Sci.* 651: 480-83, 1992. CD20 and CD5 expression in B-chronic lymphocytic leukemia.

Marx J.L. *Science* 229(4712): 455-56, 1985. Antibodies made to order.

Masucci G. et al. *Med. Oncol. Tumor Pharmacother.* 8(3): 207-20, 1991. Chemotherapy and immunotherapy of colorectal cancer.

Mazza P. et al. *Bone Marrow Trans.* 23: 1273-78, 1999. Analysis of feasibility of myeloablative therapy and autologous peripheral stem cell (PBSC) transplantation in the elderly: an interim report.

McLaughlin P. et al. *Blood* 92(10 Suppl. 1): 414a-415a, abst. No. 1712, Nov. 1998. Efficacy controls and long-term follow-up for relapsed or refractory, low-grade or follicular (R-LG/F) NHL.

McLaughlin P. et al. *Oncology* 12(12): 1763-81, 1998. Clinical status and optimal use of rituximab for B-cell lymphomas.

McLaughlin, P. et al. *Journal of Clinical Oncology* 16(8): 2825-2833. Aug. 1998. "Rituximab Chimeric Anti-CD20 Monoclonal Antibody Therapy for Relapsed Indolent Lymphoma: Half of Patients Respond to a Four-Dose Treatment Program."

Medical Encyclopedia: WBC count, available at http://www.nlm.nih.gov/medlineplus, accessed Jun. 1, 2003.

Meredith R.F. et al. *J. Nucl. Med.* 33(9): 1648-53, 1992. Dose fractionation of radiolabeled antibodies in patients with metastatic colon cancer.

Mishell B.E. et al., eds. *Selected Methods in Cellular Immunology*, San Francisco: Freeman (1980), p. 287-304. Modification and use of antibodies to label cell surface antigens.

Morrison S. et al. *Proc. Nat'l Acad. Sci. USA* 81: 6851-54, 1984. Chimeric human antibody molecules: mouse antigen-binding domains with human constant region domains.

Morrison S.L. *Science* 229: 1202-07, 1985. Transfectomas provide novel chimeric antibodies.

Multani P.S. et al. *J. Clin. Oncol.* 16(11): 3691-3710, 1998. Monoclonal antibody-based therapies for hematologic malignancies.

Munro A. *Nature* 312: 597, 1984. Uses of chimeric antibodies.

Murray J.L. et al. *J. Biol. Resp. Modifiers* 9(6): 556-63, 1990. Recombinant alpha-interferon enhances tumor targeting of an antimelanoma monoclonal antibody in vivo.

Murray J.L. et al. *J. Nucl. Med.* 26: 3328-29, 1985. The effect of radionuclide dose on imaging with indium-111-labeled anti P-97 monoclonal antibody.

Muzaffar S. et al. *J. Pak. Med. Assn.* 47(4): 106-09, Apr. 1997. Immunophenotypic analysis of non-Hodgkin's lymphoma.

Nadler L.M. et al. *Cancer Res.* 40(9): 3147-54, 1980. Serotherapy of a patient with a monoclonal antibody directed against a human lymphoma-associated antigen.

Nadler L.M. et al. *J. Clin. Invest.* 67: 134-140, 1981. A unique cell surface antigen identifying lymphoid malignancies of B cell origin.

Nadler L.M. et al. *J. I Clin. Invest.* 74(2): 332-40, 1984. B cell origin of non-T cell acute lymphoblastic leukemia. A model for discrete stages of neoplastic and normal pre-B cell differentiation.

Nadler L.M. et al. *Lancet* 2(8400): 427-31, 1984. Anti-B1 monoclonal antibody and complement treatment in autologous bone-marrow transplantation for relapsed B-cell non-Hodgkin's lymphoma.

Nakamura K. et al. *Oncology* 50(1): 35-40, 1993. Effect of alpha-interferon on anti-alpha fetoprotein-monoclonal-antibody targeting of hepatoma.

Neuberger M.S. et al. *Nature* 314: 268-70, 1985. A hapten-specific chimaeric IgE antibody with human physiological effector function.

Nguyen D.T. et al. *Eur. J. Haematol.* 62: 76-82, 1999. IDEC-C2B8 anti-CD20 (Rituximab) immunotherapy in patients with low-grade non-Hodgkin's lymphoma and lymphoproliferative disorders: evaluation of response on 48 patients.

Nielsen B. et al. *Eur. J Haematol.* 48(3): 146-51, 1992. Interferon-α-induced changes in surface antigens in a hairy-cell leukemia (JOK-1), and a Burkitt's lymphoma cell line (Daudi) during in vitro culture.

Non-Hodgkin's Lymphoma Pathologic Classification Project. *Cancer* 49(10): 2112-35, 1982. National Cancer Institute sponsored study of classifications of non-Hodgkin's lymphomas.

O'Brien S. *Genentech Onlcology and IDEC Pharmaceuticals Investigator Initiated Protocol Concept Worksheet*, 1997. Phase I-II Study of IDEC-C2B8 in CLL.

O'Brien S. *Blood* 92(10 Supp. 1): 105a (1998) abstract No. 431. Phase 1/11 Study of rituxan in chronic lymphocytic leukemia (CLL).

O'Brien S.M. et al. *J. Clin. Oncol.* 19: 2165-70, 2001. Rituximab dose-escalation trial in chronic lymphocytic leukemia.

O'Brien et al. *N. Engl. J. Med.* 330(5):319-22. Lack of effect of 2-chlorodeoxyadenosine therapy in patients with chronic lymphocytic leukemia refractory to fludarabine therapy.

Oettgen H.C. et al. *Hybridoma* 2(1): 17-28, 1983. Further biochemical studies of the human B-cell differentiation antigens B1 and B2.

Oncology Nursing Society. onsopcontent.ons.org/oes/online_ce/lymph/.05-classification.htm, retrieved Feb. 25, 2003. Current therapies and future directions in the treatment of non-Hodgkin's lymphoma.

Ozato K. et al. *J. Immunol.* 126(1): 317-21, 1981. Monoclonal antibodies to mouse MHC antigens. III. Hybridoma antibodies reacting to antigens of the H-2b haplotype reveal genetic control of isotype expression.

Panka D.J. et al. *Proc. Nat'l. Acad. Sci.* 85: 3080-84, 1988. Variable region framework differences result in decreased or increased affinity of variant anti-digoxin antibodies.

Parker B.A. et al. *Cancer Res.* 50(3): 1022s-1028s, 1990. Radioimmunotherapy of human B-cell lymphoma with $^{90}$Y-conjugated antiidiotype monoclonal antibody.

Pearson J.W. et al. *Cancer Res.* 49(18): 4990-95, 1989. Enhanced therapeutic efficacy of an immunotoxin in combination with chemotherapy against an intraperitoneal human tumor xenograft in athymic mice.

Petryk M. et al. *Oncologist* 6: 317-26, 2001. ASCO 2001: Critical commentaries: Hematologic malignancies.

Pietersz G.A. et al. *Immunol. Cell. Biol.* 65(2): 111-25, 1987. The use of monoclonal antibody conjugates for the diagnosis and treatment of cancer.

Piro L. et al. *Blood* 90(10 Suppl. 1): 510a, abst. No. 2272, 1997. RITUXAN™ (rituximab, IDEC-C2B8): Interim analysis of a phase II study of once weekly times 8 dosing in patients with relapsed low-grade or follicular non-Hodgkin's lymphoma.

Piro L.D. et al. *Ann. Oncol.* 10: 655-61, 1999. Extended Rituximab (anti-CD20 monoclonal antibody) therapy for relapsed or refractory low-grade or follicular non-Hodgkin's lymphoma.

Polyak M.J. et al. *Blood* 99: 3256-62, 2002. Alanine-170 and proline-172 are critical determinants for extracellular CD20 epitopes; heterogeneity in the fine specificity of CD20 monoclonal antibodies is defined by additional requirements imposed by both amino acid sequence and quaternary structure.

Press O. et al. *Proc. Ann. Mtg. ASCO* 5: 221, abst. No. 864, 1986. Serotherapy of malignant B cell lymphomas with monoclonal antibody 1F5 (anti-CD20).

Press O.W. *Cancer J. Sci. Amer.* 4(Suppl 2): S19-S26, Jul. 1998. Prospects for the management of non-Hodgkin's lymphomas with monoclonal antibodies and immunoconjugates.

Press O.W. et al. *Adv. Exp. Med. Biol.* 303: 91-96, 1991. Radiolabeled antibody therapy of human b cell lymphomas.

Press O.W. et al. *Blood* 69(2): 584-91, 1987. Monoclonal antibody 1F5 (anti-CD20) serotherapy of human B cell lymphomas.

Press O.W. et al. *Cancer Res.* 49(17): 4906-12, 1989. Endocytosis and degradation of monoclonal antibodies targeting human B-cell malignancies.

Press O.W. et al. *J. Clin. Oncol.* 7(8): 1027-38, 1989. Treatment of refractory non-Hodgkin's lymphoma with radiolabeled MB-1 (anti-CD37) antibody.

Press O.W. et al. *Lancet* 346(8971): 336-40, 1995. Phase II trial of 1311-B1 (anti-CD20) antibody therapy with autologous stem cell transplantation for relapsed B cell lymphomas.

Press O.W. et al. *N. Engl. J. Med.* 329(17): 1219-23, 1993. Radiolabeled-antibody therapy of B-cell lymphoma with autologous bone marrow support.

Press O.W. et al. *Proc. Ann. Mtg. ASCO* 17, abst. No. 9, May 1998. A phase I/II trial of high dose iodine-131-anti-B1 (anti-CD20) monoclonal antibody, etoposide, cyclophosphamide, and autologous stem cell transplantation for patients with relapsed B cell lymphomas.

Rai K.R. et al. (in) R. Hoffman, R., ed., *Hematology*, 2d. ed. (Churchill Livingstone), 1995. Chapter 83, pp. 1308-1319. Chronic lymphocytic leukemia.

Reff M. et al. *J. Cell. Biochem.* Suppl. 17E: 260, abst. No. T103, 1993. Depletion of B cells in vivo by a chimeric mouse human monoclonal antibody to CD20.

Reff M. et al. *Blood* 83(2):435-445, Jan. 15, 1994. Depletion of b cells in vivo by a chimeric mouse human monoclonal antibody to CD20.

Reff M.E. et al. *Blood* 83(2): 435-45, 1994. Depletion of B cells in vivo by a chimeric mouse human monoclonal antibody to CD20.

Reilly R.M. *Clin. Pharm.* 10: 359-75, 1991. Radioimmunotherapy of malignancies.

Robertson M.J. et al. *Blood* 79(9): 2229-36, 1992. Human bone marrow depleted of CD33-positive cells mediates delayed but durable reconstitution of hematopoiesis: clinical trial of MY9 monoclonal antibody-purged autografts for the treatment of acute myeloid leukemia.

Robinson et al. *Hum. Antibod. Hybridomas* 2:84-93, Apr. 1991. Chimeric mouse-human anti-carcinoma antibodies that mediate different anti-tumor cell biological activities.

Ross (ed.), Essentials of Human Physiology, 2d ed., Yearbook Medical Publishers Inc., Chicago, p. 133 (1984).

Rottenburger C. et al. *Br. J. Haematol.* 106(2): 545-52, 1999. Clonotypic CD20+ and CD19+ B cells in peripheral blood of patients with multiple myeloma post high-dose therapy and peripheral blood stem cell transplantation.

Rudikoff S. et al. *Proc. Nat'l. Acad. Sci.* 79: 1979-83, 1982. Single amino acid substitution altering antigen-binding specificity.

Sahagan B.G. et al. *J. Immunol.* 137: 1066-74, 1986. A genetically engineered murine/human chimeric antibody retains specificity for human tumor-associated antigen.

Saville, M.W. Statement of M. Wayne Saville, M.D., dated Dec. 20, 2007, submitted by applicant in Taiwan (R.O.C.) patent application No. 088119557.

Scharff M. *Harvey Lectures* 69: 125-42, 1974. The synthesis, assembly, and secretion of immunoglobulin: a biochemical and genetic approach.

Schlom J. et al. *J. Natl. Cancer Inst.* 82(9): 763-71, 1990. Advantage of dose fractionation in monoclonal antibody-targeted radioimmunotherapy.

Schulman M. et al. *Nature* 276(5685): 269-72, 1978. A better cell line for making hybridomas secreting specific antibodies.

Schulz et al., "Phase 2 study of a combined immunochemotherapy using rituximab and fludarabine in patients with chronic lymphocytic leukemia," Blood 100(9): 3115-20 (Nov. 2002).

Schwartz-Albiez R. et al. *J. Immunol.* 140(3): 905-14, 1988. The B cell-associated CD37 antigen (gp40-52). Structure and subcellular expression of an extensively glycosylated glycoprotein.

Seaver S. *Gen. Engr. News.* 19 and 21, 1994. Monoclonal antibodies in industry: more difficult than originally thought.

See-Lasley K. et al. Manual of Oncology Therapeutics. St. Louis: C.V. Mosby Co., pp. 44-71, 1981. Hodgkin's disease and non-Hodgkin's lymphoma.

Senter P.D. *FASEB J.* 4: 188-93, 1990. Activation of prodrugs by antibody-enzyme conjugates: a new approach to cancer therapy.

Senter P.D. et al. *Adv. Exp. Med. Biol.* 303: 97-105, 1991. Activation of prodrugs by antibody-enzyme conjugates.

Senter P.D. et al. *Cancer Res.* 49: 5789-92, 1989. Enhancement of the in vitro and in vivo antitumor activities of phosphorylated mitomycin C and etoposide derivatives by monoclonal antibody-alkaline phosphatase conjugates.

Shan D. et al. *Clin. Cancer Res.* 7(8): 2490-95, 2001. Synergistic effects of the fenretinide (4-HPR) and anti-CD20 monoclonal antibodies on apoptosis induction of malignant human B cells.

Sharkey R.M. et al. *Cancer Res.* 50(3): 964s-969s, 1990. Biological considerations for radioimmunotherapy.

Smalley R.V. et al. *N. Engl. J. Med.* 327(19): 1336-41, 1992. Interferon alfa combined with cytotoxic chemotherapy for patients with non-Hodgkin's lymphoma.

Smeland E.B. et al. *J. Immunol.* 138(10): 3179-84, 1987. Activation of human B cells: alternate options for initial triggering and effects of nonmitogenic concentrations of anti-IgM antibodies on resting and activated cells.

Soiffer R.J. et al. *Blood* 79(2): 517-26, 1992. Clinical and immunologic effects of prolonged infusion of low-dose recombinant interleukin-2 after autologous and T-cell-depleted allogeneic bone marrow transplantation.

Soiffer R.J. et al. *Blood* 84(3): 964-971, 1994. Effect of low-dose interleukin-2 on disease relapse after T-cell-depleted allogeneic bone marrow transplantation.

Solal-Celigny P. et al. *J. Clin. Oncol.* 16(7): 2332-38, 1998. Doxorubicin-containing regimen with or without interferon alfa-2b for advanced follicular lymphomas: final analysis of survival and toxicity in the Groupe d'Etude des Lymphomes Folliculaires 86 Trial.

Srivastava S.C. et al. *Nucl. Med. Biol. (I.J. Rad. Appl. Instrum. B)* 18(6): 589-603, 1991. Progress in research on ligands, nuclides and techniques for labeling monoclonal antibodies.

Stashenko P. et al. *J. Immunol.* 125(4): 1678-85, 1980. Characterization of Human B Lymphocyte-Specific Antigen.

Staudt L.M. et al. Manuscript from pubmedcentral at NIH, edited paper published at *Adv. Immunol.* 87: 163-208, 2005. The biology of human lymphoid malignancies revealed by gene expression profiling.

Stenbygaard et al. *Breast Cancer Research and Treatment* 25:57-63, 1993. Toremifene and tamoxifen in advanced breast cancer—a double-blind cross-over trial.

Stewart J.S.W. et al. *Int. J. Cancer Suppl.* 3: 71-76, 1988. Intraperitoneal $^{131}$I- and $^{9}$Y-labelled monoclonal antibodies for ovarian cancer: pharmacokinetics and normal tissue dosimetry.

Sun L.K. et al. *Hybridoma* 5(Suppl. 1): S17-20, 1986. Chimeric antibodies with 17-1A-derived variable and human constant regions.

Tan L.K. et al. *J. Immunol.* 135: 3564-67, 1985. A human-mouse chimeric immunoglobulin gene with a human variable region is expressed in mouse myeloma cells.

Tedder T.F. et al. *Eur. J. Immunol.* 16(8): 881-87, 1986. Antibodies reactive with the B1 molecule inhibit cell cycle progression but not activation of human B lymphocytes.

Tedder T.F. et al. *J. Immunol.* 135(2): 973-79, 1985. The B cell surface molecule B1 is functionally linked with B cell activation and differentiation.

Tedder T.F. et al. *J. Immunol.* 141(12): 4388-94, 1988. Cloning of a complementary DNA encoding a new mouse B lymphocyte differentiation antigen, homologous to the human B1 (CD20) antigen, and localization of the gene to chromosome 19.

Teeling J.L. et al. *Blood* 104:1793-1800, 2004. Characterization of new human CD20 monoclonal antibodies with potent cytolytic activity against non-Hodgkin lymphomas.

Teeling J.L. et al. *J. Immunol.* 277: 362-71, 2006. The biological activity of human CD20 monoclonal antibodies is linked to unique epitopes on CD20.

Thomas et al., "Rituximab in relapsed or refractory hairy cell leukemia," *Blood* 102(12): 3906-11 (Dec. 2003).

Tobinai K. et al. *Ann. Oncol.* 9(5): 527-34, 1998. Feasibility and pharmacokinetic study of a chimeric anti-CD20 monoclonal antibody (IDEC-C2B8, rituximab) in relapsed B-cell lymphoma. The IDEC-C2B8 Study Group.

Tsai D.E. et al. *Blood* 92(10 Suppl. 1): 415a, abst. No. 1713, Nov. 1998. Progressive intermediate grade non-Hodgkin's lymphoma after high dose therapy and autologous peripheral stem cell transplantation (PSCT) has a high response rate to rituximab.

Tsai D.E. et al. *Bone Marrow Transplant.* 24(5): 521-26, 1999. Rituximab (anti-CD20 monoclonal antibody) therapy for progressive intermediate-grade non-Hodgkin's lymphoma after high-dose therapy and autologous peripheral stem cell transplantation.

Tsai D.E. et al. *Clin. Lymphoma Myeloma* 1(1): 62-66, 2000. Progressive intermediate-grade non-Hodgkin's lymphoma after high-dose therapy and autologous peripheral stem-cell transplantation: changing the natural history with monoclonal antibody therapy.

Uckun F.M. et al. *Cancer Res.* 45(1): 69-75, 1985. Increased efficiency in selective elimination of leukemia cells by a combination of a stable derivative of cyclophosphamide and a human B-cell-specific immunotoxin containing pokeweed antiviral protein.

Uckun F.M. et al. *J. Immunol.* 134(5): 3504-15, 1985. Combined ex vivo treatment with immunotoxins and mafosfamid: a novel immunochemotherapeutic approach for elimination of neoplastic T cells from autologous marrow grafts.

Urlaub, G. et al. *Som. Cell. Mol. Genet.* 12(6): 555-66, 1986. Effect of gamma rays at the dihydrofolate reductase locus: deletions and inversions.

Valentine M.A. et al. *J. Biol. Chem.* 264: 11282-87, 1989. Phosphorylation of the CD20 phosphoprotein in resting B lymphocytes. Regulation by protein kinase C.

van der Kolk L.E. et al. *Blood* 92(10 Suppl. 1): 241b, abst. No. 4037, Nov, 1998. Chimeric anti-CD20 monoclonal antibody (rituximab) plus G-CSF in relapsed B-cell lymphoma: a phase I/II clinical trial.

van der Kolk L.E. et al. *Br. J. Haematol.* 102(1): 243, abst. No. P-0970, Jul. 1998. Chimeric anti-CD20 monoclonal antibody (rituximab) plus G-CSF in relapsed B-cell lymphoma: a phase I/II clinical trial.

van der Kolk, L.E. et al. *Blood* 92(10 Suppl. 1): 512a-513a, abst. No. 2284, 1997. Phase I/II clinical trial to evaluate the safety and efficacy of a chimeric anti-CD20 monoclonal antibody (rituximab) and G-CSF given weekly to patients with relapsed B-cell lymphoma.

Vartholomatos et al. *Acta Haernatol.* 102:94-98. 1999. Rituximab (anti-CD@) monoclonal antibody administration in a young patient with resistant B-prolymphocytic leukemia.

Venugopal P. et al. *Blood* 92(10 Suppl. 1): 247a, abst. No. 1009, Nov. 1998. Upregulation of CD20 expression in chronic lymphocytic leukemia (CLL) cells by in vitro exposure to cytokines.

Venugopal et al. *Pan Pacific Lymphoma Conference*. 1999. Cytokine-induced upregulation of CD20 antigen expression in chronic lymphocytic leukemia (CLL) cells may be limited to tumor cells [abstract].

Venugopal et al., "Effects of cytokines on CD20 antigen expression on tumor cells from patients with chronic lymphocytic leukemia," *Leuk. Res.* 24(5): 411-15 (May 2000).

Verkh L.I. et al. *Proc. Ann. Mtg. ASCO* 17: abst. No. 154, 1998. Dosimetry results of ONCOLYM™ in the treatment of refractory B cell non-Hodgkin's lymphoma (NHL).

Vey N. et al. *Leuk. Lymphoma* 221(1-2): 107-14, 1996. A pilot study of autologous bone marrow transplantation followed by recombinant interleukin-2 in malignant lymphomas.

Vose J.M. et al. *J. Clin. Oncol.* 19(2): 389-97, 2001, Phase II study of rituximab in combination with chop chemotherapy in patients with previously untreated, aggressive non-Hodgkin's lymphoma.

Wadler S. et al. *Semin. Oncol.* 19(2 Suppl. 3): 45-48, 1992. Principles in the biomodulation of cytotoxic drugs by interferons.

Wahl R.L. et al. *Proc. Ann. Mtg. ASCO* 17: 40a, abst. No. 156, May 1998. Successful retreatment of non-Hodgkin's lymphoma (NHL) with iodine-131 anti-B1 antibody.

Wahl R.L. et al. *J. Nucl. Med.* 31(5): 852, abst. No. 622, 1990. Radioimmunotherapy of B-cell lymphoma with 1131 MB-1 monoclonal antibody.

Welte K. et al. *Blood* 64: 380-85, 1984. Defective interleukin 2 production in patients after bone marrow transplantation and in vitro restoration of defective T lymphocyte proliferation by highly purified interleukin 2.

Wessels B.W. et al. *Med. Phys.* 11(5): 638-45, 1984. Radionuclide selection and model absorbed dose calculations for radiolabeled tumor associated antibodies.

White C.A. et al. *Ann. Oncol.* 10(3 Suppl): 64, abst. No. 215, 1999. Radioimmunotherapy of relapsed or refractory non-Hodgkin's lymphoma (NHL): IDEC-Y2B8 phase I/II $^{90}$yttrium trial.

White C.A. et al. *Ann. Rev. Med.* 52: 125-45, 2001. Antibody-targeted immunotherapy for treatment of malignancy.

White C.A. et al. *Blood* 87(9): 3640-49, 1996. Radioimmunotherapy of relapsed B-cell lymphoma with Yttrium 90 anti-idiotype monoclonal antibodies.

White C.A. et al. *Eur. J. Cancer* 35: S57, abst. No. 107, 1999. Zevalin™ radioimmunotherapy of relapsed or refractory non-Hodgkin's lymphoma.

Winkler U. et al. *Blood* 92(10 Suppl. 1): 285b, abst. No. 4228, Nov. 1998. Severe side effects in patients with B-cell chronic lymphocytic leukemia (CLL) and lymphocytosis treated with the monoclonal anti-CD20 antibody rituximab.

Winkler et al. *Blood* 94:2217-2224. 1999. Cytokine-release syndrome in patients with B-cell chronic lymphocytic leukemia and high lymphocyte counts after treatment with an anti-CD20 monoclonal antibody (rituximab IDEC-CB?).

Wiseman G. et al. *Blood* 92(10 Suppl. 1): 417a, abst. No. 1721, Nov. 1998. IDEC-Y2B8 radioimmunotherapy: baseline bone marrow involvement and platelet count are better predictors of hematologic toxicity than dosimetry.

Wiseman G. et al. *Cancer Biother. Radiopharm.* 13(1): 59, abst. No. 22, 1998. Radioimmunotherapy of relapsed non-Hodgkin's lymphoma (NHL) with IDEC-Y2B8 $^{90}$yttrium anti-CD20 monoclonal antibody.

Wiseman G. et al. *Cancer Biother. Radiopharm.* 13(4): 317, abst. No. 51, 1998. IDEC-Y2B8 radioimmunotherapy of relapsed non-Hodgkin's lymphoma (NHL): interim analysis.

Wiseman G. et al. *Cancer Biother. Radiopharm.* 14(4): 315, abst. No. 2, 1999. 90Yttrium labelled IDEC Y2B8 anti-CD20 radioimmunotherapy.

Wiseman G. et al. *I.J. Rad. Oncol. Biol. Phys.* 45(10 Suppl): 390, abst. No. 260, 1999. Radioimmunotherapy of relapsed or refractory non-Hodgkin's Lymphoma (NHL) with IDEC-Y2B8.

Wiseman G. et al. *Proc. Ann. Mtg. ASCO* 17, 1998. Radioimmunotherapy of relapsed non-Hodgkin's lymphoma (NHL) with IDEC-Y2B8 $^{90}$yttrium radioimmunotherapy.

Wiseman G.A. et al. *Blood* 92(10 Suppl. 1): 510a, abst.No. 2273, Nov. 1998. IDEC-Y2B8 ($^{90}$Y conjugated anti-CD20) dosimetry calculated from InIn anti-CD20 in patients with low and intermediate grade B-cell non-Hodgkin's lymphoma (NHL) emphasis on bone marrow (BM).

Wiseman G.A. et al. *Blood* 94(10 Suppl. 1): 92a, abst. No. 403, 1999. Zevalin™ biodistribution and dosimetry estimated normal organ absorbed radiation doses are not affected by prior therapy with rituximab.

Wiseman G.A. et al. *Clin. Cancer Res.* 5(Suppl.): 3281s-3286s, 1999. Radioimmunotherapy of relapsed non-Hodgkin's lymphoma with Zevalin, a $^{90}$Y-labeled anti-CD20 monoclonal antibody.

Wiseman G.A. et al. *I.J. Oncol. Biol. Phys.* 42(1 Suppl.): 130, abst. No. 11, 1998. IDEC-Y2B8 ($^{90}$yttrium ibritumomab tiuxetan) radioimmunotherapy safety results in relapsed or chemotherapy refractory non-Hodgkin's lymphoma patients treated at reduced doses because of pre-existing thrombocytopenia.

Wiseman G.A. et al. *J. Nucl. Med.* 38(5 Suppl.): 251, abst. No. 1062, 1997. Y-90 anti-CD20 monoclonal antibody (IDEC-Y2B8) dosimetry calculated from In-111 anti-CD20 in patients with low and intermediate grade B-cell non-Hodgkin's lymphoma.

Wiseman G.A. et al. *J. Nucl. Med.* 39(5 Suppl.): 185P, abst. No. 836, 1998. Whole-body gamma camera image quantification from multiple camera types for radioisotope therapy dosimetry.

Wiseman G.A. et al. *J. Nucl. Med.* 39(5 Suppl.): 69P, abst. No. 267, 1998. Non-Hodgkin's lymphoma tumor and bone marrow radiation doses from radioimmunotherapy with IDEC-Y2138 yttrium-90 anti-CD20 monoclonal antibody.

Wiseman G.A. et al. *J. Nucl. Med.* 40(1 Suppl .): 64P, abst. No. 260, 1999. Final dosimetry results of IDEC-Y2B8 phase I/II $^{90}$yttrium radioimmunotherapy trial in non-Hodgkin's lymphoma (NHL).

Wiseman G.A. et al. *Proc. Ann. Mg. ASCO* 18: 4a, abst. No. 13, 1999. Therapeutic index of IDEC-Y2B8 radioimmunotherapy: up to 850 fold greater radiation dose to tumor than normal organs.

Witherspoon R.P. et al. *Semin. Hematol.* 21(1): 2-10, 1984. Immunologic reconstitution after human marrow grafting.

Witzig T. et al. *Blood* 90(10 Suppl. 1): 586a, abst. No. 2606, 1997. IDEC-Y2B8 $^{90}$yttrium anti-CD20 radioimmunotherapy of relapsed non-Hodgkin's lymphoma (NHL): interim results of a phase I/II trial.

Witzig T. et al. *Blood* 92(10 Suppl. 1): 417a, abst. No. 1722, Nov. 1998. IDEC-Y2B8 radioimmunotherapy: responses in patients with splenomegaly.

Witzig T.E. et al. *Blood* 94(10 Suppl. 1): 92a, abst. No. 400, 1999. Reduced-dose ZEVALIN™ radioimmunotherapy for relapsed or refractory B-cell non-Hodgkin's lymphoma (NHL) patients with pre-existing thrombocytopenia: report of interim results of a phase II trial.

Witzig T.E. et al. *J. Clin. Oncol.* 17(12): 3793-3803, 1999. Phase I/II trial of IDEC-Y2B8 radioimmunotherapy for treatment of relapsed or refractory CD20(+) B-cell non-Hodgkin's lymphoma.

Witzig T.E. et al. *J. Clin. Oncol.* 20(15): 3262-69, 2002. Treatment with ibritumomab tiuxetan radioimmunotherapy in patients with rituximab-refractory follicular non-Hodgkin's lymphoma.

Witzig T.E. et al. *J. Clin. Oncol.* 20: 2453-63, 2002. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma.

Witzig T.E. et al. *J. Immunother.* 21(6): 463, abst. No. 2805, 1998. IDEC-Y2B8 radioimmunotherapy of relapsed or refractory non-Hodgkin's lymphoma.

Witzig T.E. et al. *Proc. Ann. Mtg. ASCO* 18: 41a, abst. No. 152, 1999. Commonly used response criteria for non-Hodgkin's lymphoma (NHL) applied to IDEC-Y2B8 radioimmunotherapy trial: importance of "normal" lymph node size.

Witzig T.E. et al. *Blood* 94(10 Suppl. 1): 631a, abst. No. 2805, 1999. Prospective randomized controlled study of ZEVALIN™ (IDEC-Y2B8) radioimmunotherapy compared to rituximab immunotherapy for B-cell NHL: report of interim results.

Witzig T.E. et al. *Am. J. Clin. Paihol.* 101: 312-17, 1994. Measurement of the intensity of cell surface antigen expression in B-cell chronic lymphocytic leukemia.

Yang H. et al. *Am. J. Hematol.* 62: 247-50, 1999. Tumor lysis syndrome occurring after the administration of rituximab in lymphoproliferative disorders: high-grade non-Hodgkin's lymphoma and chronic lymphocytic leukemia.

Yokota S. et al. *Cancer Res.* 50: 32-37, 1990. Synergistic potentiation of in vivo antitumor activity of anti-human T-leukemia immunotoxins by recombinant α-interferon and daunorubicin.

Zhou X. et al. *Chinese Pharm. J.* 30(8): 453-54, 1995. 细胞因子疗法在肿瘤治疗中的应用(English translation of abstract provided.).

A Patient's Guide: Treating Low-Grade or Follicular (Indolent) NHL with Rituxan, pp. 1-12 (2007) http://www.rituxan.com/lymphoma/images/RITUXAN_PatientLowgradeFollicularGuide.pdf.

Alas et al., "Rituximabb inactives signal transducer and activation of transcription 3 (STAT3) activity in B-non-Hodgkin's lymphoma through inhibition of the interleukin 10 autocrine/paracrine loop and results in down-regulation of Bcl-2 and sensitization to cytotoxic drugs" Cancer Res 61(13):5137-5144 (Jul. 1, 2001).

Batata et al., "Relationship between Chronic Lymphocytic Leukemia and Small Lymphocytic Lymphoma: A Comparative Study of Membrane Phenotypes in 270 Cases" Cancer 70(3):625-632 (Aug. 1, 1992).

Bowen et al., "Subcutaneous campath-1H in fludarabine-resistant/relapsed chronic lymphocytic and B-prolypohocytic leukemia" Brit J Haematol 96:617-619 (1997).

Brown et al., "Treatment of B-Cell Lymphomas With Anti-Idiotype Antibodies Alone and In Combination With Alpha Interferon" Blood 73(3):651-661 (Feb. 15, 1989).

Byrd et al., "Addition of rituximab to fludarabine may prolong progression-free survival and overall survival in patients with previously untreated chronic lymphocytic leukemia: an updated retrospective comparative analysis of CALGB 9712 and CALGB 9011" Blood 105(1):49-53 (Jan. 1, 2005).

Byrd et al., "Old and new therapies in chronic lymphocytic leukemia: now is the time for a reassessment of therapeutic goals" Semin Oncol 25(1):65-74 (Feb. 1998).

Byrd et al., "Randomized phase 2 study of flurdarabine with concurrent versus swquential treatment with rituximab in symptomatic, untreated patients with B-cell chronic lymphocytic leukemia: results from Cancer and Leukemia Group B 9712 (CALGB 9712)" Blood 101(1):6-14 (Jan. 1, 2003).

U.S. Appl. No. 60/107,685, filed Nov. 9, 1998, pp. 1-22 (Jan. 13, 2000).

Chan, "The new world health organization classification of lymphomas: the past, the present and the future" Hematological Oncology 19:129-150 (2001).

Cheson et al., "Guidelines for Clinical Protocols for Chronic Lymphocytic Leukemia: Recommendations of the National Cancer Institute-Sponsored Working Group" Am J Hematol 29:152-163 (1988).

Chiorazzi et al., "Evolving View of he In-Vivo Kinetics of Chronic Lmphocytic Leukemia B Cells" Hematology:273-278 (2006).

Coiffier et al., "A multicenterm randomized phase II study of rituximab (chimeric anti-CD20 mAb) at two dosages in patiens with relapsed of refractory intermediate or high-grade NHL (IHG-NGL) or in elderly patients in first-line therapy" Blood (Abstract 2271), 90(10 Suppl 1):510a (Nov. 15, 1997).

Committee for medicinal products for human use post-authorisation summary of positive opinion for MABTHERA (rituximab) with select pages from Annex I: Summary of Product Characteristics regarding Rituximab, Doc. Ref. EMEA/CHMP/48585/2009, pp. 1-2 (Jan. 22, 2009).

de Lima et al., "Chronic Lymphocytic Leukemia in the Young Patient" Semin Oncol 25(1):107-116 (Feb. 1998).

DeNardo et al., "Increased survival associated with radiolabeled Lym-1 for non-Hodgkin's lymphoma and chronic lymphocytic leukemia" Cancer 80(12):2706-2711 (Dec. 15, 1997).

Du et al., "Structure of the Fab fragment of therapeutic antibody Ofatumumab provides insights into the recognition mechanism with CD20" Mol Immunol 46:2419-2423 (2009).

Eichhorst et al., "Fludarabine plus cyclophosphamide versus fludarabine alone in first-line therapy of younger patients with chronic lymphocytic leukemia" Blood 107:885-891 (2006).

FDA News Release: FDA Approves Rituxan to Treat Chronic Lymphocytic Leukemia, pp. 1 (Feb. 18,2010).

Flinn et al., "Phase III trial of fludarabine plus cyclophosphamide compared with fludarabine for patients with previously untreated chronic lymphocytic leukemia: US Intergroup Trial E2997" J Clin Oncol 25(7):793-798 (Mar. 1, 2007).

Foerster Wintrobe'S Clinical Hematology "Chronic Lymphocytic Leukemia" (Chapter 78), G. Richard Lee et al., 9th edition, Philadelphia:Lea & Febiger, vol. 2:2034-2053 (1993).

Foon et al., "Chemoimmunotherapy with low-dose fludarabine and cyclophosphamide and high dose rituximab in previously untreated patients with chronic lymphocytic leukemia" J Clin Oncol 27(4):498-503 (Feb. 1, 2009).

Foon et al., "Effects of Monoclonal Antibody Therapy in Patients With Chronic Lymphocytic Leukemia" Blood 64(5):1085-1093 (Nov. 1984).

Foon, "Treatment of B-Cell Lymphoma With Monoclonal Anti-Idiotype Antibody" New Engl J Med 307(11):686-687 (Sep. 9, 1982).

Genentech and IDEC Pharmaceuticals to Collaborate on Anti-CD20 Monoclonal Antibody for B-cell Lymphomas, pp. 1-2 (press release Mar. 3,1995).

Gidlof et al., "Antibodies Are Capable of Directing Superantigen-Mediated T Cell Killing of Chronic B Lymphocytic Leukemia Cells" Leukemia 9:1534-1542 (1995).
GlaxoSmithKline, GSK and Genmab receive accelerated approval for Arzerra (press release), pp. 1-3 (Oct. 26,2009).
Hale et al., "Therapeutic Potential of Rat Monoclonal Antibodies: Isotype Specificity of Antibody-Dependent Cell-Mediated Cytotoxicity with Human Lymphocytes" J Immunol 134(5):3056-3061 (May 1985).
Hallek et al., "Addition of rituximab to fludarabine and cyclophosphamide in patients with chronic lymphocytic leukaemia: a randomised, open-label, phase 3 trial" Lancet 376:1164-1174 (2010).
Hallek et al , "Immunochemotherapy with Fludarabine (F), Cyclophosphamide (C), and Rituximab (R) (FCR) Versus Fludarabine and Cyclophosphamide (FC) Improves Response Rates and Progression-Free Survival (PFS) of Previously Untreated Patients (pts) with Advanced Chronic Lymphocytic Leukemia (CLL)" Blood (Abstract 325 from 2008 ASH Annual Meeting Abstracts), 112(11):125 (Nov. 16, 2008).
Harrison's Principles of Internal Medicine "Chronic Lymphocytic Leukemia" Kurt J. Isselbacher et al., 13th edition, New York:McGraw-HIll, Inc., vol. 2:1771-1774 (1994).
Hercher et al., "A Multicentric Study of 41 Cases of B-Prolymphocytic Leukemia: Two Evolutive Forms" Leukemia Lymphoma 42(5):981-987 (2001).
IDEC Pharmaceuticals Corporation Annual Report for the Fiscal Year Ended Dec. 31, 1997, pp. 1-50 (1997).
Johnson et al., "Multicentre prospective randomised trial of fludarabine versus cyclophosphamide, doxorubicin, and prednisone (CAP) for treatment of advanced-stage chronic lymphocytic leukaemia. The French Cooperative Group on CLL" Lancet 347:1432-1438 (May 25, 1996).
Johnston Wintrobe'S Clinical Hematology "Chronic Lymphocytic Leukemia" (Chapter 93), G. Richard Lee et al., 10th edition, Baltimore:Williams & Wilkins, vol. 2:2405-2427 ( 1999).
Kaminski et al., "I-131 Anti-B 1 Antibody for Previously Untreated Follicular Lymphoma (FL): Clinical and Molecular Remissions" Proc Am Soc Clin Oncol (Abstract 6), 17:2a (1998).
Keating et al., "Early Results of a Chemoimmunotherapy Regimen of Fludarabine, Cyclophosphamide, and Rituximab As Initial Therapy for Chronic Lymphocytic Leukemia" J Clin Oncol 23(18):4079-4088 (Jun. 20, 2005).
Keating et al., "Long-Term Follow-Up of Patients with Chronic Lymphocytic Leukemia (CLL) Receiving Fludarabine Regimens as Initial Therapy" Blood 9(4):1165-1171 (Aug. 15, 1998).
Knox et al., "Randomized controlled study of 131I-Anti-B1 versus unlabeled-Anti-Bl monoclonal antibody in patients with chemotherapy refractory low grade non-Hodgkin's lymphoma" International Journal of Radiation Oncology Biology Physics (Abstract 2172), 39(2 (Supplement)):326 (1997).
List of different EP patent families assigned to IDEC that relate to Rituximab, pp. 1 (2011).
Maloney et al., "IDEC-C2B8 Anti-CD20 Antibody: Results of Long-Term Follow-up of Relapsed NHL Phase II Trial Patients" Blood (Abstract 205), 88(10 Suppl 1 (Part 1 of 2)):54a (Nov. 15, 1996).
Maloney et al., "IDEC-C2B8: Final Report on a Phase II Trial in Relapsed Non-Hodgkin's Lymphoma" Blood (Abstract 661), 84(10 Suppl 1):169a (Nov. 15, 1994).
Maloney et al., "Initial Report on a Phase I/II Multiple Dose Clinical Trial of IDEC-C2B8 (Chimeric Anti-CD20) in Relapsed B Cell Lymphoma" Proceedings of ASCO (Abstract 993), 13:304 (Mar. 1994).
Maloney et al., "Newer treatments for non-Hodgkin's lymphoma: Monoclonal antibodies" Oncology 12(10 Suppl 8):63-76 (Oct. 2, 1998) http://www.cancernetwork.com/display/article/10165/72098.
Maloney, "Advances in Immunotherapy of Hematologic Malignancies" Curr Opin Hematol 5(4):237-243 (1998).
Manero et al., "Update of Results of the Combination of Fludarabine, Cyclophosphamide and Rituximab for Previously Treated Patients with Chronic Lymphocytic Leukemia (CLL)" Blood (Abstract 2650), 93:633a (2001).

Mason et al., "Antibody L26 Recognizes an Intracellular Epitope on the B-Cell-Associated CD20 Antigen" Am J Pathol 136(6):1215-1222 (Jun. 1990).
McLaughlin et al., "IDEC-C2B8 anti-CD20 antibody: final report on a phase III pivotal trial in patients (PTS) with relapsed low-grade or follicular lymphoma (LG/F NHL)" Blood (Abstract 349), 88(10 Suppl 1 (Part 1 of 2)):90a (Nov. 15, 1996).
McLaughlin et al., "Pharmacokinetics (PK) and Pharmacodynamics (PD) of the Anti-CD20Antibody (MAB) IDEC-C2B8 in Patients (PTS) with Relapsed Low-Grade or Follicular Lymphoma (LG/F NHL)" Blood (Abstract 350), 88(10 Suppl 1 (Part 1 of 2)):90a (Nov. 15, 1996).
Montserrat et al., "B-cell chronic lymphocytic leukemia: Recent progress in biology, diagnosis, and therapy" Ann Oncol 8(Suppl 1):S93-S101 (1997).
Nguyen et al., "IDEC-C2B8 anti-CD20 immunotherapy in patients with non-Hodgkin's lymphoma (NHL): hematological effects in the bone marrow and peripheral blood" Blood (Abstract 2276), 90(10 Suppl 1 (Part 1 of 2)):511a (Nov. 15, 1997).
Nguyen et al., "IDEC-C2B8 Anti-CD20 Phase II Trial: Results on Bone Marrow and Peripheral Blood Tumor Response in Patients with Low Grade Non-Hodgkin's Lymphoma/Lymphoproliferative Disorders" Blood (Abstract 2277), 90(10 Suppl 1 (Part 1 of 2)):511a (Nov. 15, 1997).
O'Brien et al., "Advances in the Biology and Treatment of B-Cell Chronic Lymphocytic Leukemia" Blood 85(2):307-318 (Jan. 15, 1995).
Office Action Response to European Patent Office Regarding IDEC Pharmaceuticals Corporation's EP Patent Application 99960232.9, pp. 1-5 (May 27, 2004).
Onishi et al., "Chronic Lymphocytic Leukemia" Sogo Rinsho (English Translation of Japanese Office Action Attached), 46(Special Issue):552-556 (1997).
Osterborg et al., "Humanized CD52 Monoclonal Antibody Campath-1H as First-Line Treatment in Chronic Lymphocytic Leukaemia" Brit J Haematol 93:151-153 (1996).
Osterborg et al., "Phase II Multicenter Study of Human CD52 Antibody in Previously Treated Chronic Lymphocytic Leukemia" J Clin Oncol 15(4):1567-1574 (Apr. 1997).
Parker, B., Clinical Review of BLA Reference No. BLA 97/0260 and BLA 97/0244, BLA reference # BLA 97/0260 (IDEC) and BLA 97/0244 (Genentech), Rituxan® product, pp. 1-40 (Nov. 25, 1992).
Piro, "Treatment of Chronic Lymphocytic Leukemia" XXVIth World Congress of the International Society of Haematology, Singapore, pp. 1-8 (Aug. 25-29, 1996).
Polyak et al., "Identification of a Cytoplasmic Region of CD20 Required for Its Redistribution to a Detergent-Insoluble Membrane Compaitment" J Immunol 161:3242-3248 (1998).
Press et al., "Radioimmunotherapy of B Cell Lymphomas" Ann Oncol (Abstract 106), 7( Suppl 3):33 (1996).
Rawstron et al., "Monoclonal B-cell lymphocytosis and chronic lymphocytic leukaemia" New Engl J Med 359(6):575-583 (Aug. 7, 2008).
Reichert et al., "Monoclonal antibody successes in the clinic" Nature Biotechnology 23(9):1073-1078 (Sep. 2005).
Reichert, "Metrics for antibody therapeutics development" MAbs 2(6):695-700 (2010).
Rituxan (Rituximab) package insert, pp. 1-2 (Nov. 1997).
Rituxan (rituximab) package insert, pp. 1-8 (revision date Jan. 2011).
Rituxan® Draft Labeling Text, pp. 1-46 (Feb. 28, 2006) http://www.accessdatafda.gov/drugsatfda_docs/label/2006/103705s5230-s52311bl.pdf.
Robak et al., "Rituximab plus fludarabine and cyclophosphamide prolongs progression-free survival compared with fludarabine and cyclophosphamide alone in previously treated chronic lymphocytic leukemia" J Clin Oncol 28(10):1756-1765 (Apr. 1, 2010).
Robak et al., "Rituximab, Fludarabine, and Cyclophosphamide (R-FC) Prolongs Progression Free Survival in Relapsed or Refractory Chronic Lymphocytic Leukemia (CLL) Compared with FC Alone: Final Results from the International Randomized Phase III REACH Trial" Blood 112:Iba-1 (Nov. 2008).
Rogers et al., "Clearance of BCL-2 (t14;18) from Peripheral Blood (PB) and Bone Marrow (BM) in Patients (PTS) with Relapsed Low- Grade or Follicular (IWF:A-D) Lymphoma (NHL) Following Single-Agent Therapy with the Chimeric Anti-CD20 Antibody (MAB) IDEC-C2B8" Ann Oncol (Abstract 108), 7(Suppl 3):34 (1996).

Scott, "Rituximab: a new therapeutic monoclonal antibody for non-Hodgkin's lymphoma" Cancer Pract. 6(3): 195-197 (1998).

Search results for the word 'hence'. Search done on WordNet lexical database by Princeton University., pp. 1 (May 2, 2011).

Smolej, "Modern concepts in the treatment of chronic lymphocytic leukemia" Hematology 14(5):249-254 (2009).

Stamenkovic et al., "Analysis of Two cDNA Clones Encoding the B Lymphocyte Antigen CD20 (B1, Bp35), A Type III Integral Membrane Protein" J Exp Med 167:1975-1980 (Jun. 1988).

Tedder et al. "Isolation and structure of a cDNA encoding the B1 (CD20) cell-surface antigen of human B lymphocytes" P Natl Acad Sci USA 85(1):208-212 (Jan. 1988).

Tedder et al. Leucocyte Typing IV "Structure of the CD20 antigen and gene of human and mouse B-cells: use of transfected cell lines to examine the Workshop panel of antibodies" Knapp et al., Oxford:Oxford University Press,:48-50 (1989).

Tefferi et al., "Heterogeneity and Clinical Relevance of the Intensity of CD20 and Immunoglobulin Light-Chain Expression in B-Cell Chronic Lymphocytic Leukemia" Am J Clin Pathol 106:457-461 (1996).

Vervoordeldonk et al., "Preclinical studies with radiolabeled monoclonal antibodies for treatment of patients with B-cell malignancies" Cancer 73(3 SUPPL Supplement):1006-1111 (Feb. 1, 1994).

Wierda et al., "Chemoummunotherapy With Fludarabine, Cyclophosphamide, and Rituximab for Relapsed and Refractory Chronic Lymphocytic Leukemia" J Clin Oncol 23(18):4070-4078 (Jun. 20, 2005).

Wierda et al., "Combined Fludarabine, Cyclophosphamide, and Rituximab Achieves a High Complete Remission Rate as Initial Treatment for Chronic Lymphocytic Leukemia" Blood (Abstract 3210), 98:771a (2001).

Wikipedia page regarding body surface area, pp. 1-3 (webpage last modified Mar. 30, 2011) http://en.wikipedia.org/wiki/Body_surface_area.

Wikipedia page regarding body weight, pp. 1-3 (Webpage last modified May 18, 2011) http://en.wikipedia.org/wiki/Body_weight.

Wilhelm et al., "First-line therapy of advanced chronic lymphocytic leukemia" Leukemia 11 (Suppl 2):S14-S18 (1997).

Wilmes et al., "T-cell activation after treatment with the anti-CD20 antibody rituximab detected by FACS analysis" Ann Hematol (Abstract 660), 77(Suppl II):S166 (1998).

Zimmerman et al., "Studies of Leukocyte Kinetics in Chronic Lymphocytic Leukemia" Blood 31(3):277-291 (Mar. 1968).

Byrd et al., "The Addition of Rituximab to Fludarabine Significantly Improves Progression-Free and Overall Survival in Previously Untreated Chronic Lymphocytic Leukemia (CLL) Patients," Blood (Abstract 245), 102(11): 73a (2003).

TREATMENT OF CHRONIC LYMPHOCYTIC LEUKEMIA USING ANTI-CD20 ANTIBODIES

RELATED APPLICATIONS

This application is a continuation of U.S. application Ser. No. 09/436,347, filed Nov. 9, 1999, now allowed; which claims benefit under 35 U.S.C. §119(e) to U.S. provisional application Ser. No. 60/107,658, filed Nov. 9, 1998, now lapsed. Each of these prior applications is incorporated herein by reference in its entirety herein.

FIELD OF THE INVENTION

The present invention is directed to the treatment of hematologic malignancies associated with high numbers of circulating tumor cells by the administration of a therapeutically effective amount of a chimeric or humanized antibody that binds to the B-cell surface antigen Bp35 (CD20).

BACKGROUND OF THE INVENTION

The use of antibodies to CD20 as diagnostic and/or therapeutic agents for B-cell lymphoma has previously been reported. CD20 is a useful marker or target for B-cell lymphomas as this antigen is expressed at very high densities on the surface of malignant B-cells, i.e., those B-cells wherein unabated proliferation can lead to B-cell lymphomas.

CD20 or Bp35 is a B-lymphocyte-restricted differentiation antigen that is expressed during early pre-B-cell development and remains until plasma cell differentiation. It is believed that the CD20 molecule may regulate a step in the B-cell activation process which is required for cell cycle initiation and differentiation. Moreover, as noted, CD20 is expressed at very high levels on neoplastic ("tumor") B-cells.

Previous reported therapies involving anti-CD20 antibodies have involved the administration of a therapeutic anti-CD20 antibody either alone or in conjunction with a second radiolabeled anti-CD20 antibody, or a chemotherapeutic agent.

In fact, the Food and Drug Administration has approved the therapeutic use of one such therapeutic anti-CD20 antibody, RITUXAN® (rituximab), for use in treatment of relapsed and previously treated low-grade non-Hodgkin's lymphoma (NHL). Also, the use of RITUXAN® (rituximab) in combination with a radiolabeled murine anti-CD20 antibody has been suggested for the treatment of B-cell lymphoma.

However, while anti-CD20 antibodies and, in particular, RITUXAN® (rituximab) have been reported to be effective for treatment of B-cell lymphomas, such as non-Hodgkin's lymphoma, it would be beneficial if effective antibody treatments for other malignancies could be developed. More specifically, it would be beneficial if anti-CD20 antibodies could be used for treating other types of malignancies.

BRIEF DESCRIPTION OF THE INVENTION

Toward that end, the present inventors have developed a novel treatment for hematologic malignancies characterized by a high number of tumor cells in the blood involving the administration of a therapeutically effective amount of an anti-CD20 antibody. In the preferred embodiments, such anti-CD20 antibody will comprise a chimeric, humanized, or human anti-human CD20 antibody. Examples of such hematologic malignancies include B-pro-lymphocytic leukemia (B-PLL), chronic lymphocyte leukemia (CLL), and transformed non-Hodgkin's lymphoma.

Thus, it is an object of the invention to provide a novel treatment for hematologic malignancies comprising the administration of an anti-CD20 antibody.

It is a more specific object of the invention to provide a novel treatment for B-prolymphocytic leukemia (B-PLL), chronic lymphocytic leukemia (CLL) or transformed non-Hodgkin's lymphoma comprising the administration of an anti-CD20 antibody.

It is an even more specific object of the invention to treat B-prolymphocytic leukemia (B-PLL) or chronic lymphocytic leukemia (CLL) comprising administration of a therapeutically effective amount of RITUXAN® (rituximab).

DETAILED DESCRIPTION OF THE INVENTION

The invention involves the discovery that hematologic malignancies and, in particular, those characterized by high numbers of tumor cells in the blood may be effectively treated by the administration of a therapeutic anti-CD20 antibody. These malignancies include, in particular, CLL, B-PLL and transformed non-Hodgkin's lymphoma.

This discovery is surprising notwithstanding the reported great success of RITUXAN® (rituximab) for the treatment of relapsed and previously treated low-grade non-Hodgkin's lymphoma. In particular, this discovery is surprising given the very high numbers of tumor cells observed in such patients and also given the fact that such malignant cells, e.g., CLL cells, typically do not express the CD20 antigen at the high densities which are characteristic of some B-cell lymphomas, such as relapsed and previously-treated low-grade non-Hodgkin's lymphomas. Consequently, it could not have been reasonably predicted that the CD20 antigen would constitute an appropriate target for therapeutic antibody therapy of such malignancies.

Treatment of hematologic malignancy, such as CLL, B-PLL and transformed non-Hodgkin's lymphoma, according to the invention will comprise the administration of a therapeutically effective amount of an anti-CD20 antibody, which administration may be effected alone or in conjunction with other treatment(s), e.g., chemotherapy, radiotherapy (e.g., whole body irradiation, or treatment with radiolabeled antibodies). In addition, combination therapy with cytokines may be useful to upregulate CD20 on the surface of the lymphoma cells.

In the preferred embodiment, the anti-CD20 antibody will bind CD20 with high affinity, i.e., ranging from $10^{-5}$ to $10^{-9}$M. Preferably, the anti-CD20 antibody will comprise a chimeric, primate, PRIMATIZED®, human, or humanized antibody. Also, the invention embraces the use of antibody fragments, e.g., Fab's, Fv's, Fab's, F(ab)$_2$, and aggregates thereof.

A chimeric antibody is intended to refer to an antibody with non-human variable regions and human constant regions, most typically rodent variable regions and human constant regions.

A PRIMATIZED® antibody refers to an antibody with primate variable regions, e.g., complementarity-determining regions (CDRs), and human constant regions. Preferably, such primate variable regions are derived from an Old World monkey.

A humanized antibody refers to an antibody with substantially human framework and constant regions, and non-human CDRs. "Substantially" refers to the fact that humanized antibodies typically retain at least several donor framework residues (of non-human parent antibody from which CDRs are derived).

Methods for producing chimeric, primate, PRIMATIZED®, humanized, and human antibodies are well known in the art. See, e.g., U.S. Pat. No. 5,530,101, issued to Queen et al, U.S. Pat. No. 5,225,539, issued to Winter et al, U.S. Pat. Nos. 4,816,397 and 4,816,567, issued to Boss et al, and Cabilly et al, respectively, all of which are incorporated by reference in their entirety.

The selection of human constant regions may be significant to the therapeutic efficacy of the subject anti-CD20 antibody. In the preferred embodiment, the subject anti-CD20 antibody will comprise human, gamma 1, or gamma 3 constant regions and, more preferably, human gamma 1 constant regions. The use of gamma 1 anti-CD20 antibodies as therapeutics is disclosed in U.S. Pat. No. 5,500,362, issued to Robinson et al.

Methods for making human antibodies are also known and include, by way of example, production in SCID mice, and in vitro immunization.

As noted, a particularly preferred chimeric anti-CD20 antibody is RITUXAN® (rituximab), which is a chimeric gamma 1 anti-human CD20 antibody. The complete nucleic acid sequence encoding this antibody and the corresponding amino acid sequences of the heavy chain and light chain variable domains may be found in U.S. Pat. No. 5,736,137, which is incorporated by reference in its entirety. This antibody, which is produced in a proprietary CHO cell expression system commercialized by IDEC Pharmaceuticals Corporation, may be made by a CHO cell transfectoma comprising the vector DNA present in the *E. coli* host cell deposited on Nov. 4, 1992, under the provisions of the Budapest Treaty at the American Type Culture Collection (ATCC), University Boulevard, Manassas, Va. 20110-2209, under accession no. 69119. This deposit was determined to be viable and will be replaced should it become non-viable during the term of deposit. This deposit was made irrevocably available upon issuance of U.S. Pat. No. 5,736,137 and is available without restriction from the ATCC. This deposit will also be available without restriction during the lifetime of any patent that may issue based on this application.

The subject anti-CD20 antibody will be administered by various routes of administration, typically parenteral. This is intended to include intravenous, intramuscular, subcutaneous, rectal, and vaginal administration, with intravenous infusion being preferred.

The anti-CD20 antibody will be formulated for therapeutic usage by standard methods, e.g., by addition of pharmaceutically acceptable buffers, e.g., sterile saline, sterile buffered water, propylene glycol, and combinations thereof.

Effective dosages will depend on the specific antibody, condition of the patient, age, weight, or any other treatments, among other factors. Typically effective dosages will range from about 0.001 to about 30 mg/kg body weight, more preferably from about 0.01 to 25 mg/kg body weight, and most preferably from about 0.1 to about 20 mg/kg body weight.

Such administration may be effected by various protocols, e.g., weekly, bi-weekly, or monthly, dependent on the dosage administered and patient response. Also, it may be desirable to combine such administration with other treatments, e.g., radioactive therapy, both targeted and non-targeted, chemotherapies, and lymphokine or cytokine administration, e.g., interleukins, interferons, TNFs, colony stimulating factors, etc.

Typically, treatment will be effected weekly, for about 2 to 10 weeks, more typically about 4 weeks. A particularly preferred dosage regimen will comprise administration of about 375 mg/m$^2$ weekly for a total of four infusions. Also, stepped-up dosing schedules may be even more preferable.

If radiation is used in conjunction with the therapeutic anti-CD20 antibody, it is preferred that an yttrium-labeled anti-CD20 antibody be utilized, such as the one disclosed in U.S. Pat. No. 5,736,137, incorporated by reference in its entirety herein. This antibody, [$^{90}$Y]-2B8-MX-DTPA, has reported efficacy in the treatment of B-cell lymphoma. The hybridoma that produces the 2B8 antibody was deposited at the American Type Culture Collection under accession no. HB 11388 on Jun. 22, 1993, under the provisions of the Budapest Treaty, and was made irrevocably available upon issuance of U.S. Pat. No. 5,736,137, without any restrictions. This hybridoma was found to be viable and will be replaced during the lifetime of any patent that issues based on this application, should it become non-viable.

A particularly preferred chemotherapeutic regimen that may be used in conjunction with the subject antibody immunotherapy comprises CHOP chemotherapy, which comprises the administration of a combination of cyclophosphamide, doxorubicin, vincristine, and prednisone. Other known chemotherapeutics include methotrexate, cisplatin, toremifene, and tamoxifen.

The following examples are not intended, nor are they to be construed, as limiting the invention. The examples are intended to provide clinical evidence in support of the efficacy of the invention.

EXAMPLE 1

Two patients in whom we noted rapid reduction of blood tumor cells, which was associated with severe pulmonary infusion-related toxicity and thrombocytopenia, were studied. Also, two additional patients were collected from physician-submitted reports of adverse events related to RITUXAN® (rituximab) treatment. Pretreatment characterization of these patients included a median age of 60 years (range 26-73) with the diagnosis of B-prolymphocytic leukemia (B-PLL), chronic lymphocytic leukemia (CLL), or transformed non-Hodgkin's lymphoma. All of these patients had elevated leukocyte counts as a consequence of blood tumor involvement, bulky adenopathy and organomegaly. All four patients developed a unique syndrome of severe infusion-related reactions characterized by fever, rigors, bronchospasm with associated hypoxemia, requiring temporary cessation of RITUXAN® (rituximab) therapy. Concurrent with these symptoms, a rapid decrement in circulating tumor cell load (mean pretreatment 98×10$^3$ L; range 73-132 vs. mean post-treatment 11×10$^3$ L; range 37-24.6) with mild electrolyte evidence of rapid tumor lysis was observed. Thrombocytopenia, a finding not commonly associated with RITUXAN® (rituximab) therapy, was noted in all four patients (mean pretreatment 145×10$^3$ L; range 57-277 vs. mean post-treatment Sn×10$^9$/L; range 2-120), requiring transfusion in one case. Symptoms of this syndrome required hospitalization but resolved with supportive care. Subsequent RITUXAN® (rituximab) treatment were well tolerated in all patients.

Two subsequent patients with CLL have been treated with high blood tumor counts utilizing stepped-up dosing (100 mg day 1 followed by the rest of therapy on day 1) with demonstrated efficacy, thrombocytopenia but minimal infusion-related toxicity. RITUXAN® (rituximab) administration in patients with hematologic malignancies who have blood tumor cell involvement may be associated with a higher frequency of severe initial infusion-related reactions and thrombocytopenia mandating careful clinical monitoring. Given the preliminary activity of RITUXAN® (rituximab) in these patients, future studies in CLL and PLL, utilizing a stepped-up dosing schedule, are to be conducted.

EXAMPLE 2

Unlabeled immunoglobulins (monoclonal antibodies, Mabs) are attractive for the treatment of NHL as they may: mediate cytotoxicity with complement (CDC) or effector cells (ADCC); effect apoptosis; be less toxic, less immunogenic and possibly more effective than toxin- or drug-conjugated Mabs; not require the complex procedures needed for radiolabeled Mab therapy (radioimmunotherapy, RIT), and not produce the myelosuppression typical of high-dose RIT.

Until recently, use of Mabs in the treatment of hematologic malignancies has been limited. However, the chimeric anti-CD20 Mab, RITUXAN® (rituximab), has a low toxicity profile and significant clinical efficacy and is now approved by the U.S. Food and Drug Administration (November 1997) and in the E.U. (June 1998) for the treatment of relapsed or refractory, low-grade or follicular (R-LG/F) NHL. In a single-agent phase III clinical trial, of 166 patients with R-LG/F NHL treated with RITUXAN® (rituximab) at 375 mg/m² weekly for four infusions (study 102-05), the overall response rate (ORR) was 48% (6% complete response (CR) and 42% partial response (PR)). Median time to progression for responders was 13.1 months and duration of response was 11.2 months. Median circulating B-lymphocyte counts dropped to zero following the first dose. CD3, CD4, CD8 and NK cell counts remained unchanged. B-cell recovery in peripheral blood began at 6-9 months and was complete by 9-12 months. No significant changes in serum complement levels were noted. The mechanism for action remains unresolved with CDC, ADCC, apoptosis and/or others being considered. In spite of the absence of a clinical/laboratory correlation, the contribution of CDC cannot be discounted. We have seen a correlation between higher absolute NK cell count at baseline and response to the Mab.

| Cell Type | # Patients CR + PR | Abs. Count | # Patients NR | Abs. Count | P-value |
|---|---|---|---|---|---|
| NK | 98 | 180 | 15 | 98 | 0.02 |
| MK + ANC | 98 | 185 | 15 | 102 | 0.02 |
| ANC | 101 | 3.7 | 15 | 3.4 | 0.40 |
| CD3+ | 98 | 761 | 15 | 576 | 0.37 |
| Platelets | 101 | 187 | 15 | 206 | 0.32 |

Note:
N = 166 patients from study 102-05, and 37 from 102-06. Abs. Count: NK, CD3 = cells/mm³; ANC, Pts. = cells × 10³/mm³. P value for the difference between Abs. Counts.

ADCC may be an important mechanism for the clinical activity seen in patients treated with RITUXAN® (rituximab). Agents which enhance effector cell number and activity may synergize with the Mab. Studies of RITUXAN® (rituximab) in combination with cytokines, e.g., Il-2, G-CSF, GM-CSF, INF, are also ongoing.

EXAMPLE 3

Phase I/II Study of RITUXAN® (Rituximab) in CLL

RITUXAN® (rituximab) is a monoclonal antibody targeting CD20 that has significant activity in the treatment of low-grade lymphoma (LGL). When given at a dosage of 375 mg/m² weekly for four weeks the response rate in relapsed patients was 43% (McClaughlin et al., KOO, Vol. 14, 1998). Patients with small lymphocytic lymphoma (SLL) had lower response rates (13%) than patients with other subtypes of LGL and lower serum levels of RITUXAN® (rituximab). Reduced response seen in SLL could be related to lower density of CD20 antigen and/or higher circulating B-cell counts. Both factors would be expected to impact (negatively) on response seen in CLL.

In an attempt to maximize activities in CLL we are conducting a Phase I/II study. All patients receive a first dose of 375 mg/m² to minimize infusion related side effects. Subsequent weekly dosages (3) remain the same but are given at an increased dose level. Sixteen patients have been treated at dosages of 500-1500 mg/m². Median age was 66 years (range, 25-78). Eighty-one percent had end-stage III-IV disease. Median white blood cell count was 40×10⁹/L (range, 4-200), Hgb 11.6 g/dl (range, 7.7-14.7), platelets 75×10⁹/L (range, 16-160), median $\beta_2$ microglobulin was 4.5 mg/L (range, 3.1-9.2). Median numbers of prior therapies was 2.5 (range 1-9). Sixty percent of patients were refractory to treatment. Two patients developed severe hypertension with the first dose (375 mg/m²); another one received further therapy. Toxicity at subsequent escalated dosages has been mild although no patient at the 1500 mg/m² dose level has been fully evaluated. Eight patients have completed therapy (4 at 500 mg/m², 3 at 650 mg/m², 1 at 825 mg/m²). One patient treated at 560 mg/m² achieved full remission. One patient has progressive lymphocytosis on treatment and all other patients had reduction in peripheral blood lymphocytosis but less effect on lymph nodes. Dose escalation studies are ongoing.

EXAMPLE 4

Use of Cytokines to Upregulate the Expression of CD20

Another approach to improving response in CLL patients is to upregulate the CD20 antigen using cytokines. In an in vitro study, mononuclear cells from CLL patients were incubated for 24 hours with various cytokines. Flow cytometry results showed significant up-regulation by IL-4, GM-CSF, and TNF-alpha. (Venugopal P, Sivararnan S, Huang X, Chopra H, O'Brein T, Jajeh A, Preisler H. Upregulation of CD20 expression in chronic lymphocytic leukemia (CLL) cells by in vitro exposure to cytokines. Blood 1998; 10:247a.) In fact, recent data suggest that the upregulation of CD20 observed on CLL cells may be limited to tumor cells (Venogopal et al. Poster—PanPacific Lymphoma meeting, June 1999. Cytokine-induced upregulation of CD20 antigen expression in chronic lymphocytic leukemia (CLL) cells may be limited to tumor cells). Preliminary data also suggest that interferon alpha also upregulates CD20 on CLL cells after only 24 hours when applied at a concentration of 500 to 1000 U/ml.

Thus, by administering certain cytokines to CLL patients prior to or concurrently with administration of RITUXAN® (rituximab), the expression of CD20 on the surface of malignant B-cells may be upregulated, thereby rendering CD20, as well as other cell surface markers such as CD19, a more attractive target for immunotherapy.

A collaborative study has been initiated to test for optimal cytokine doses for CD20 upregulation in vivo. The study protocol involves treating ten patients initially with GM-CSF at 250 mcg/m² SQ QD X 3, ten patients with IL-4 mcg/kg SQ QD X 3, and ten patients with G-CSF at 5 mcg/kg SQ QD X 3. Mononuclear cells will be separated by FICOLL® (sucrose-epichlorohydrin copolymer) Hypaque centrifugation for apoptotic studies to determine if upregulation of CD20 translates to enhanced killing of tumor cells by RITUXAN® (rituximab).

EXAMPLE 5

Combination Antibody and Chemotherapy Protocol

Antibody treatment of CLL can be combined with other conventional chemotherapeutic treatments known to be useful for the treatment of CLL. The most frequently used single agent for CLL is chlorambucil (LEUKERAN®), given either as 0.1 mg/kg daily or 0.4 to 1.0 mg/kg every 4 weeks. Chlorambucil is often combined with oral prednisone (30 to 100 mg/m$^2$/d), which is useful in the management of autoimmune cytopenias. Cyclophosphamide is an alternative to chlorambucil, the usual dose being 1-2 g/m$^2$ every 3-4 weeks together with vincristine and steroids (e.g., COP regimen).

Various drug combinations have been used for CLL, including COP (cyclophosphamide, Oncovin, and prednisone), and CHOP (these three drugs plus doxorubicin). Fludarabine has shown an effect in the treatment of CLL, and gave an ORR of 50% in a group of patients treated with 25-30 mg/m$^2$/d every 3-4 weeks. See www.cancernetwork.com. Some patients have been shown to be refractory for fludarabine. Such patients may also be resistant to 2-CdA because often, patients who are refractory to fludarabine are also refractory to 2-CDA (O'Brien et al. N. Engl. J. Med. 330: 319-322 (1994)).

Hence, anti-CD20 antibody therapy will be particularly useful for patients who are refractory or who have relapsed after treatment with chemotherapeutic drugs. RITUXAN® (rituximab) therapy may also be combined with radiotherapy in these patients. TBI with a low fraction size of 15 cGy to total doses of 75 to 150 cGy has been shown to be effective in about one-third of patients.

A Phase II trial is currently being conducted by CALGB in CLL patients. RITUXAN® (rituximab) and fludarabine are administered concurrently, followed by RITUXAN® (rituximab) consolidation versus fludarabine induction followed by RITUXAN® (rituximab). The goals of the study are (1) to determine in fludarabine treated CLL patients the complete response (CR) rate and toxicity profile of concurrent and consolidative RITUXAN® (rituximab) therapy (Arm I) and of consolidative RITUXAN® (rituximab) therapy (Arm II); (2) to assess the CR rate in patients receiving concurrent therapy with RITUXAN® (rituximab) and fludarabine (the inductive phase of Arm I); (3) to assess the frequency of conversion of a partial response (PR) to a CR or stable disease to either PR or CR in CLL patients receiving consolidative therapy with RITUXAN® (rituximab); (4) to follow the effects of therapy with RITUXAN® (rituximab) and fludarabine on the immunologic markers CD4, CD8, IgG, IgA and IgM; and (5) to examine progression-free survival and overall survival in Arms I and II.

Although the present invention has been described in some detail by way of illustration and example, for purposes of clarity and understanding it will be apparent that certain changes and modifications may be practical within the scope of the appended claims.

The invention claimed is:

1. A method of treating chronic lymphocytic leukemia (CLL) in a human patient, comprising administering rituximab to the patient in an amount effective to treat the CLL, wherein the rituximab is administered to the patient at a dosage of 500 mg/m$^2$.

2. The method of claim 1 further comprising administering a chemotherapeutic regimen to the patient.

3. The method of claim 2 wherein the chemotherapeutic regimen comprises fludarabine.

4. The method of claim 2 wherein the chemotherapeutic regimen comprises cyclosphosphamide.

5. The method of claim 1 wherein the rituximab is administered weekly.

6. The method of claim 1 wherein the rituximab is administered bi-weekly.

7. The method of claim 1 wherein the rituximab is administered monthly.

8. The method of claim 1 which does not include treatment with a radiolabeled anti-CD20 antibody.

9. A method of treating chronic lymphocytic leukemia (CLL) in a human patient, comprising administering rituximab to the patient in an amount effective to treat the CLL, wherein the rituximab is administered to the patient at dosages of 500 mg/m$^2$, and further comprising administering a chemotherapeutic regimen to the patient, wherein the chemotherapeutic regimen comprises fludarabine and cyclophosphamide.

* * * * *